(12) United States Patent
Remmers et al.

(10) Patent No.: US 6,752,150 B1
(45) Date of Patent: Jun. 22, 2004

(54) VENTILATORY STABILIZATION TECHNOLOGY

(76) Inventors: John E. Remmers, Box 12, Site 23, R.R. 12, Calgary Alberta (CA), T3E 6W3; Eric A. Hajduk, 7531 Fountain Road SE., Calgary Alberta (CA), T2H 0W9; Ronald S. Platt, 3413 Eighth Street SE., Calgary Alberta (CA), T2G 3A4

(*) Notice: Subject to any disclaimer, the term of this patent is extended or adjusted under 35 U.S.C. 154(b) by 0 days.

(21) Appl. No.: 09/498,504

(22) Filed: Feb. 3, 2000

Related U.S. Application Data
(60) Provisional application No. 60/118,616, filed on Feb. 4, 1999.

(51) Int. Cl.[7] ............................................. A61M 16/00
(52) U.S. Cl. ............................. 128/204.18; 128/204.21
(58) Field of Search ...................... 128/204.18, 204.21, 128/204.23, 204.26, 205.23, 202.22

(56) References Cited

U.S. PATENT DOCUMENTS

| | | | | |
|---|---|---|---|---|
| 3,889,671 A | * | 6/1975 | Baker ........................ | 128/206 |
| 5,109,839 A | * | 5/1992 | Blasdell et al. ......... | 128/203.12 |
| 5,503,146 A | * | 4/1996 | Froehlich et al. ...... | 128/204.23 |
| 5,537,997 A | * | 7/1996 | Mechlenburg et al. .. | 128/204.23 |
| 5,540,219 A | | 7/1996 | Mechlenburg | |
| RE35,339 E | * | 10/1996 | Rapoport ............... | 128/204.18 |
| 5,560,354 A | * | 10/1996 | Berthon-Jones et al. ........................ | 128/205.25 |
| 5,572,993 A | * | 11/1996 | Kurome et al. ........ | 128/204.23 |
| 5,598,838 A | * | 2/1997 | Servidio et al. ....... | 128/204.23 |
| 5,605,151 A | * | 2/1997 | Lynn ........................ | 128/633 |
| 5,645,053 A | * | 7/1997 | Remmers et al. ...... | 128/204.23 |
| 5,657,752 A | * | 8/1997 | Landis et al. .......... | 128/207.13 |
| 5,682,878 A | * | 11/1997 | Ogden .................... | 128/204.23 |
| 5,687,715 A | * | 11/1997 | Landis et al. .......... | 128/207.18 |
| 5,694,923 A | * | 12/1997 | Hete et al. .............. | 128/204.18 |
| 5,740,795 A | | 4/1998 | Brydon | |
| 5,752,510 A | * | 5/1998 | Goldstein ............... | 128/207.18 |
| 5,794,615 A | * | 8/1998 | Estes ...................... | 128/204.23 |
| 5,803,066 A | * | 9/1998 | Rapoport et al. ...... | 128/204.23 |
| 5,865,173 A | * | 2/1999 | Froehlich ............... | 128/204.23 |
| 5,895,360 A | | 4/1999 | Christopherson | |
| 5,906,203 A | | 5/1999 | Klockseth et al. | |
| 5,944,680 A | | 8/1999 | Christopherson et al. | |
| 5,947,115 A | * | 9/1999 | Lordo et al. ........... | 128/200.24 |
| 5,970,975 A | * | 10/1999 | Estes et al. ............. | 128/204.23 |
| 6,000,396 A | * | 12/1999 | Melker et al. ......... | 128/204.21 |
| 6,012,455 A | * | 1/2000 | Goldstein ............... | 128/207.18 |
| 6,015,388 A | | 1/2000 | Sackner et al. | |
| 6,029,660 A | * | 2/2000 | Calluaud et al. ....... | 128/200.21 |
| 6,029,665 A | | 2/2000 | Berthon-Jones | |
| 6,041,780 A | * | 3/2000 | Richard et al. ........ | 128/204.18 |
| 6,085,747 A | | 7/2000 | Axe et al. | |
| 6,091,973 A | | 7/2000 | Colla et al. | |

(List continued on next page.)

FOREIGN PATENT DOCUMENTS

| | | | |
|---|---|---|---|
| EP | o788805 A2 | * | 8/1997 |
| WO | WO 98/12965 | | 4/1998 |
| WO | WO 99/61088 | | 12/1999 |

OTHER PUBLICATIONS

Xie, et al. (1997) "Effect of Inhaled CO2 and Added Dead Space on Idiopathic Central Sleep Apnea," American Physiological Society.

Primary Examiner—Weilun Lo
Assistant Examiner—Teena Mitchell

(57) ABSTRACT

A system for reducing central sleep apnea (CSA) is described in which certain methods of increasing a patient's rebreathing during periods of the sleep cycle are used. By increasing rebreathing during periods of overbreathing, the over-oxygenation which typically results from the overbreathing period can be reduced, thus reducing the compensating underbreathing period and effectively reducing the loop gain associated with the central sleep apnea.

82 Claims, 17 Drawing Sheets

U.S. PATENT DOCUMENTS

| | | | |
|---|---|---|---|
| 6,099,479 A | 8/2000 | Christopherson et al. | |
| 6,105,575 A | 8/2000 | Estes et al. | |
| 6,123,082 A | 9/2000 | Berthon-Jones | |
| 6,126,657 A | 10/2000 | Edwards et al. | |
| 6,135,106 A * | 10/2000 | Dirks et al. | 128/204.23 |
| 6,213,119 B1 * | 4/2001 | Brydon et al. | 128/204.18 |
| 6,238,351 B1 * | 5/2001 | Orr et al. | 600/532 |
| 6,269,811 B1 * | 8/2001 | Duff et al. | 128/204.18 |
| 6,286,508 B1 * | 9/2001 | Remmers et al. | 128/204.18 |
| 6,299,581 B1 * | 10/2001 | Rapoport et al. | 128/204.21 |
| 6,336,454 B1 * | 1/2002 | Farrell et al. | 128/200.24 |
| 6,345,619 B1 * | 2/2002 | Finn | 128/204.21 |
| 6,349,724 B1 * | 2/2002 | Burton et al. | 128/204.18 |
| 6,360,741 B2 * | 3/2002 | Truschel | 128/202.22 |
| 6,363,933 B1 * | 4/2002 | Berthon-Jones | 128/200.24 |
| 6,367,474 B1 * | 4/2002 | Berthon-Jones et al. | 128/204.18 |
| 6,374,824 B1 * | 4/2002 | Thornton | 128/201.26 |
| 6,397,845 B1 * | 6/2002 | Burton | 128/204.23 |
| 6,398,739 B1 * | 6/2002 | Sullivan et al. | 600/529 |
| 6,427,689 B1 * | 8/2002 | Estes et al. | 128/204.18 |
| 6,435,181 B1 * | 8/2002 | Jones et al. | 128/204.18 |
| 6,467,483 B1 * | 10/2002 | Kopacko et al. | 128/207.12 |
| 6,532,959 B1 * | 3/2003 | Berthon-Jones | 128/204.23 |

* cited by examiner

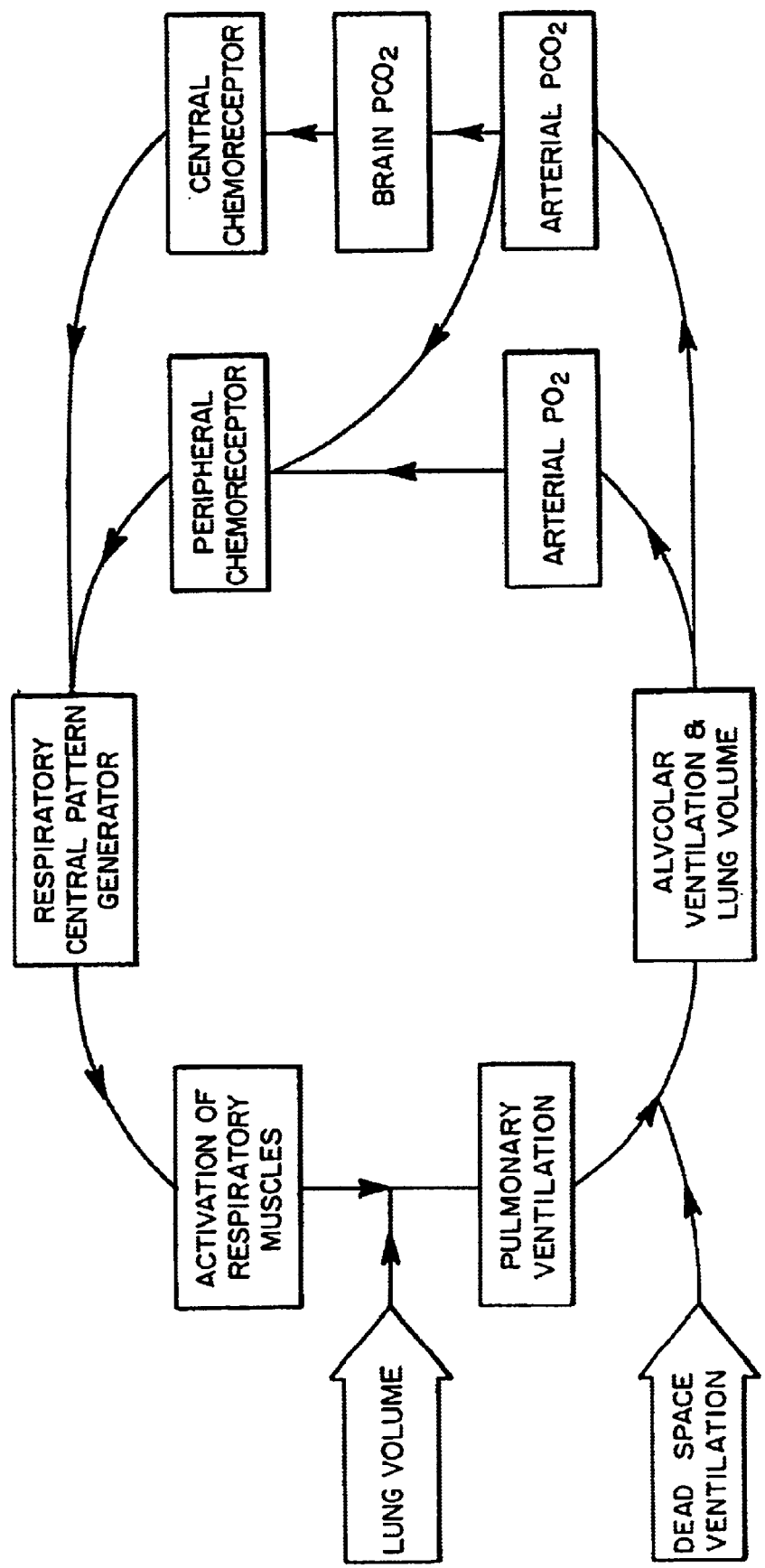
FIG_1

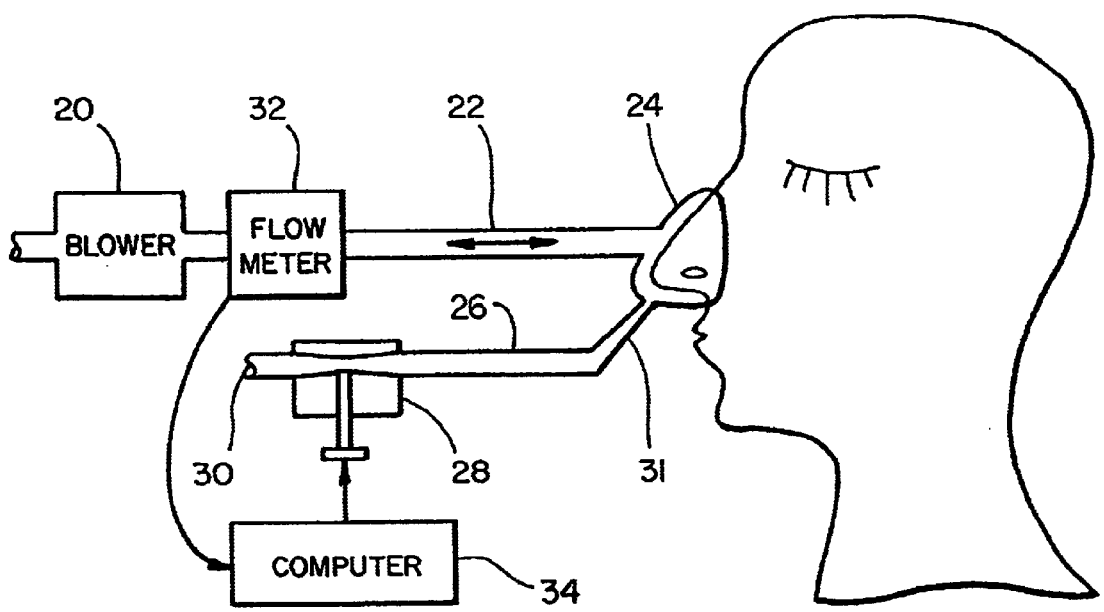
FIG_2
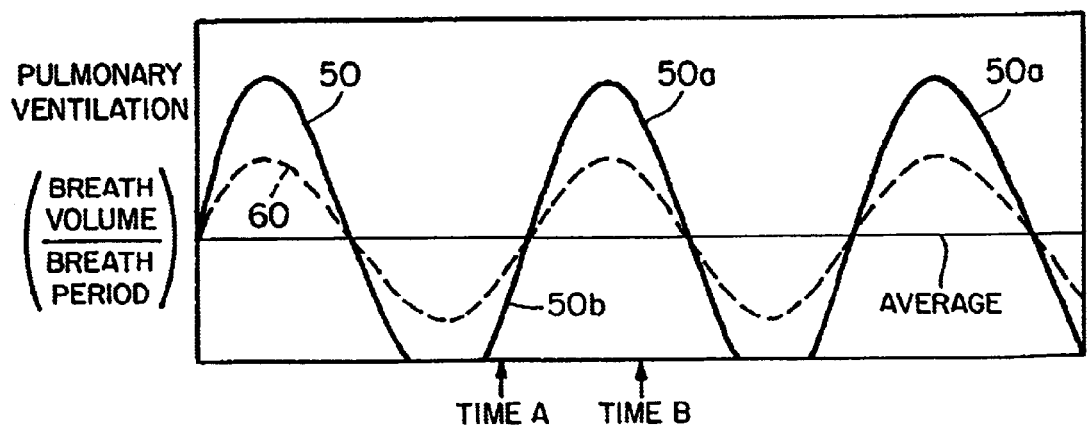
FIG_3

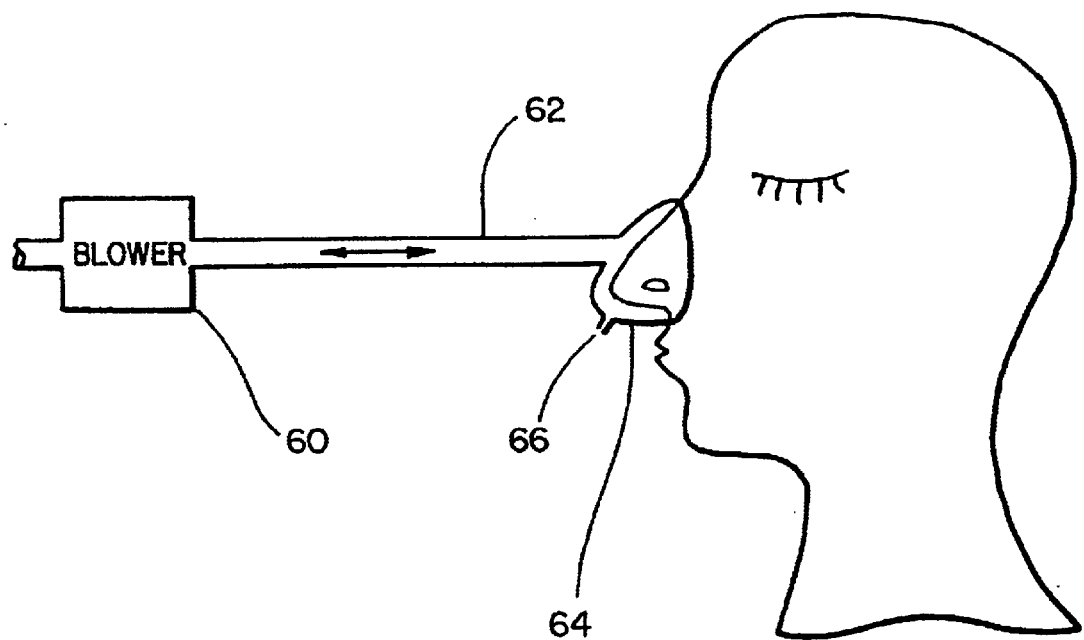
*FIG_4A*
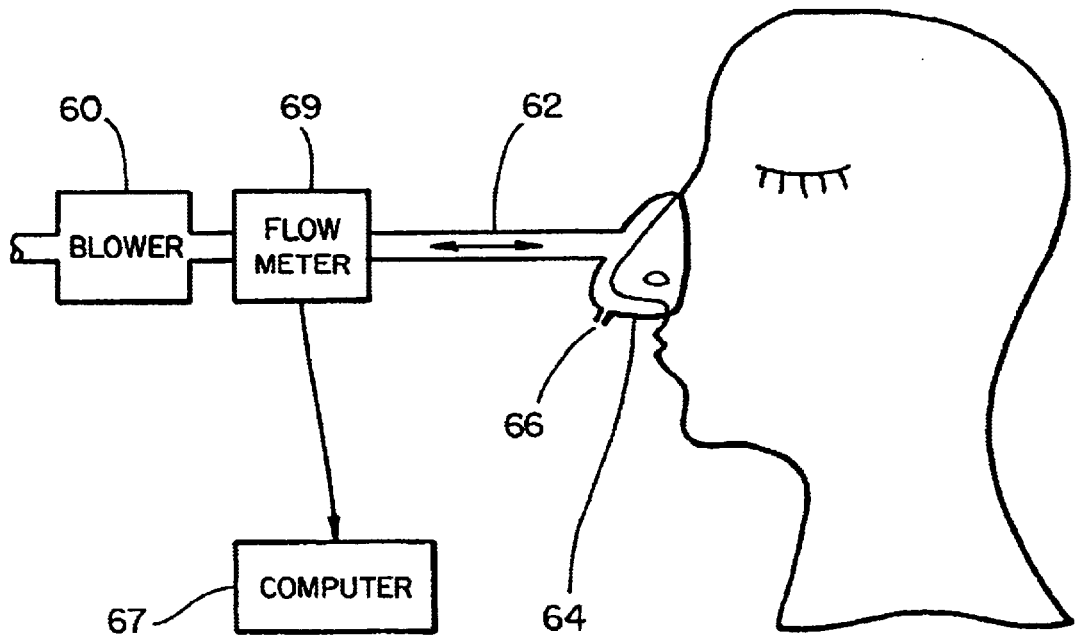
*FIG_4B*

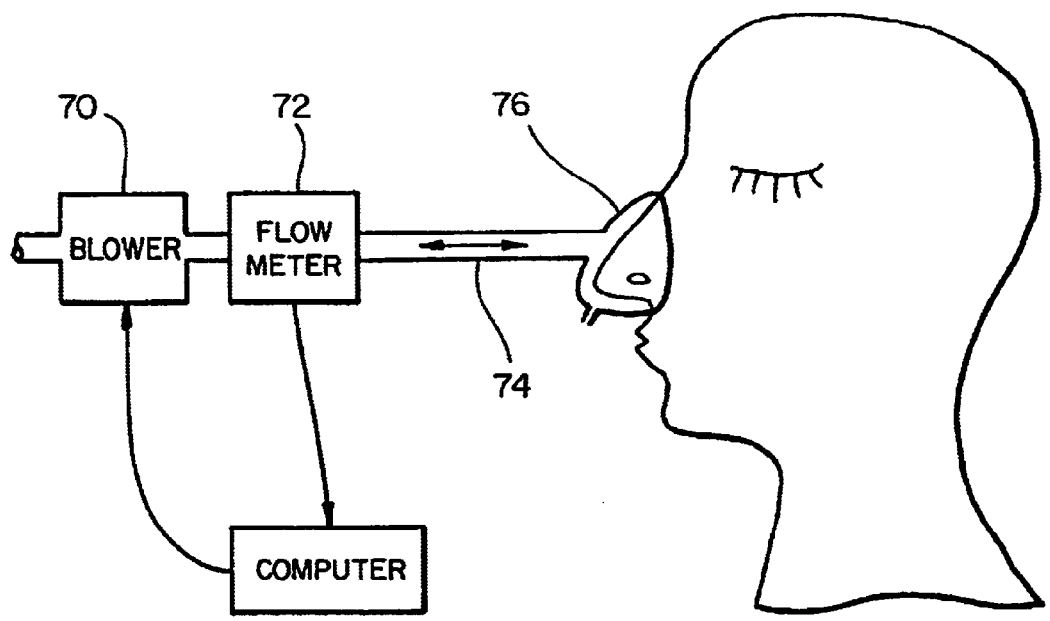
FIG_5
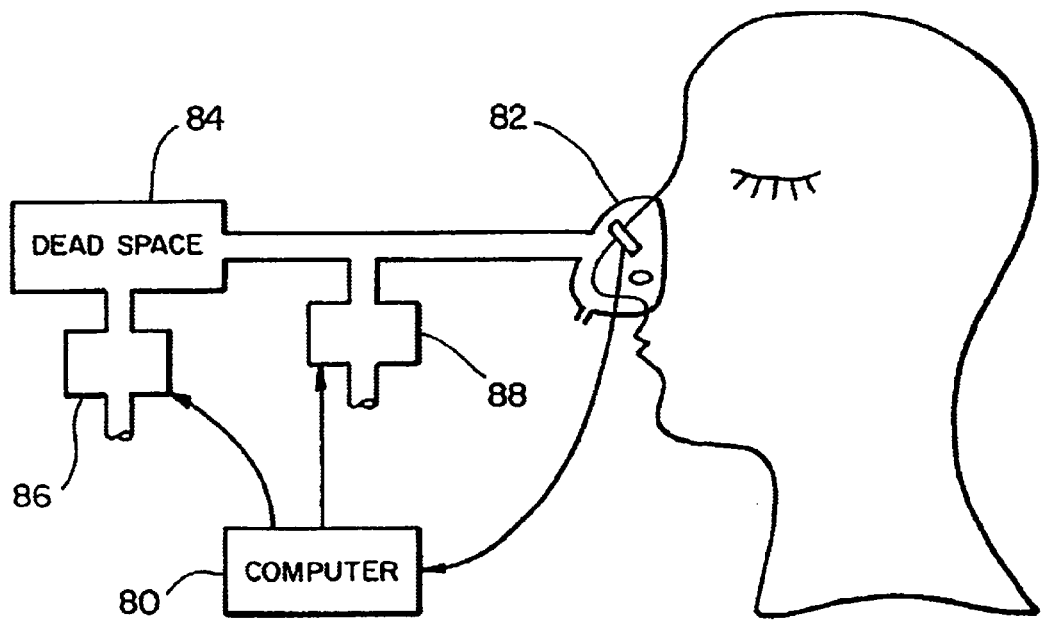
FIG_6

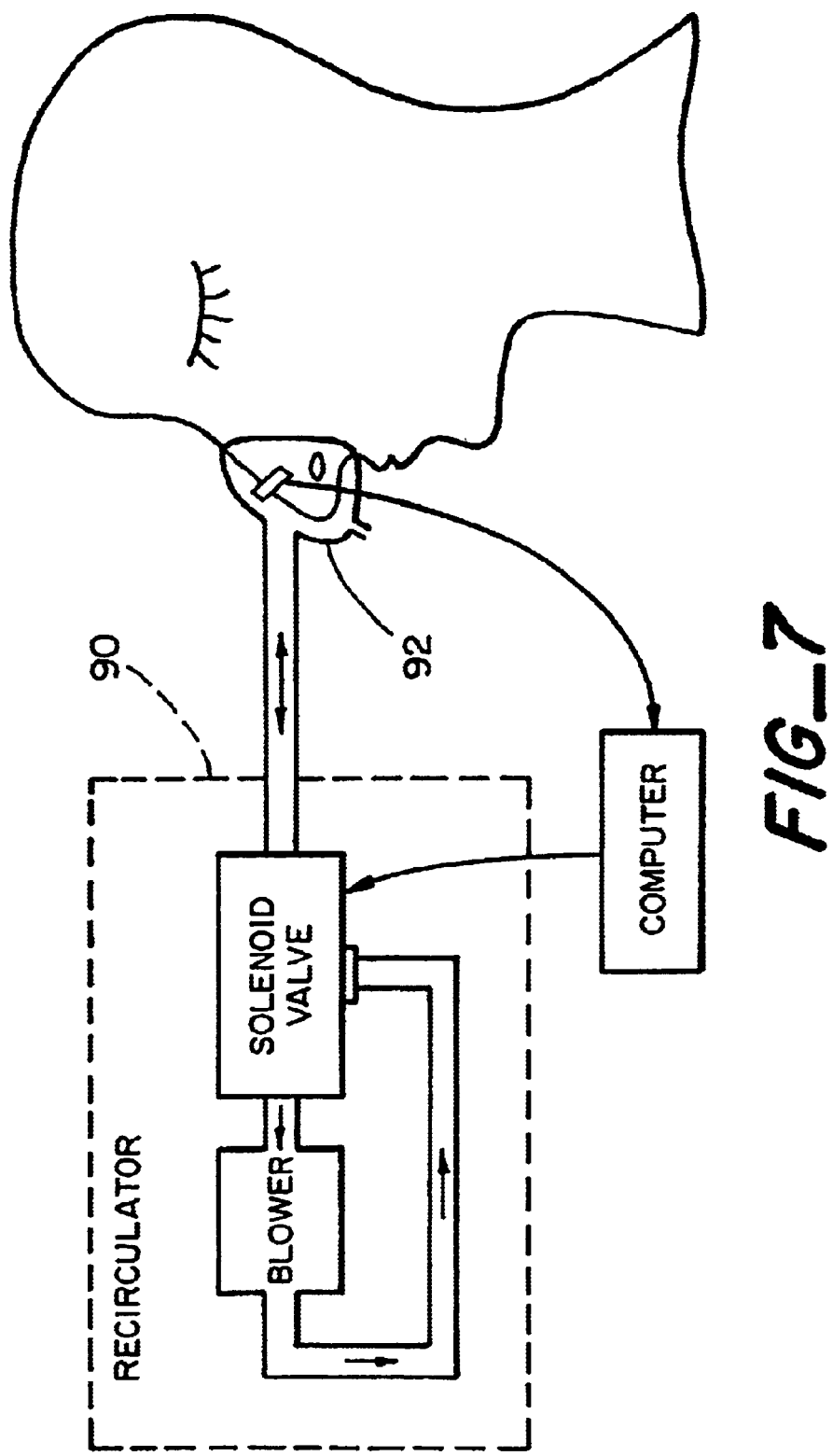
FIG_7

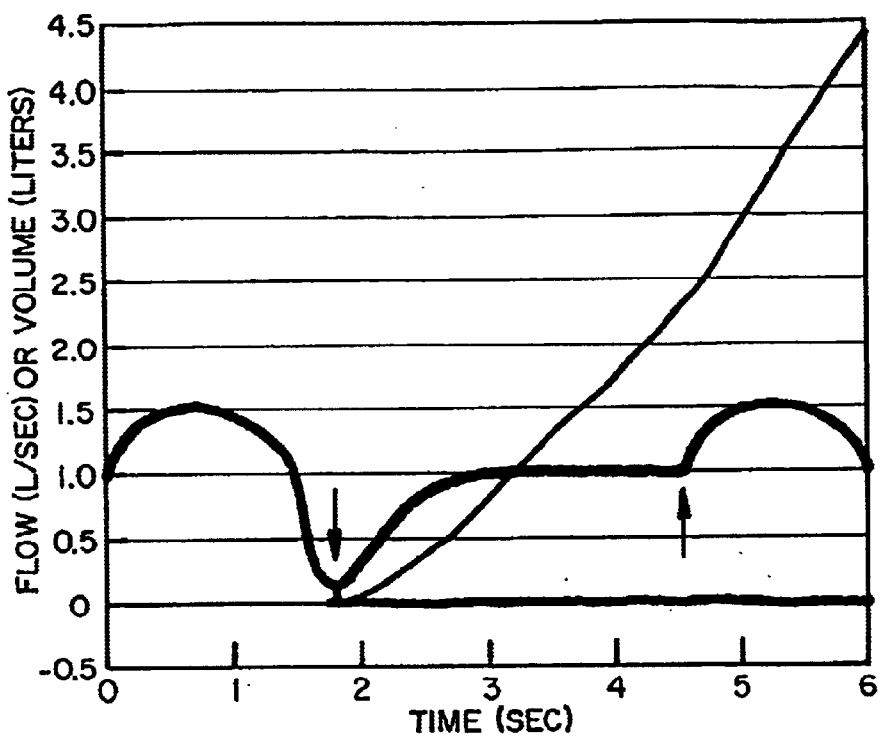
FIG_8A
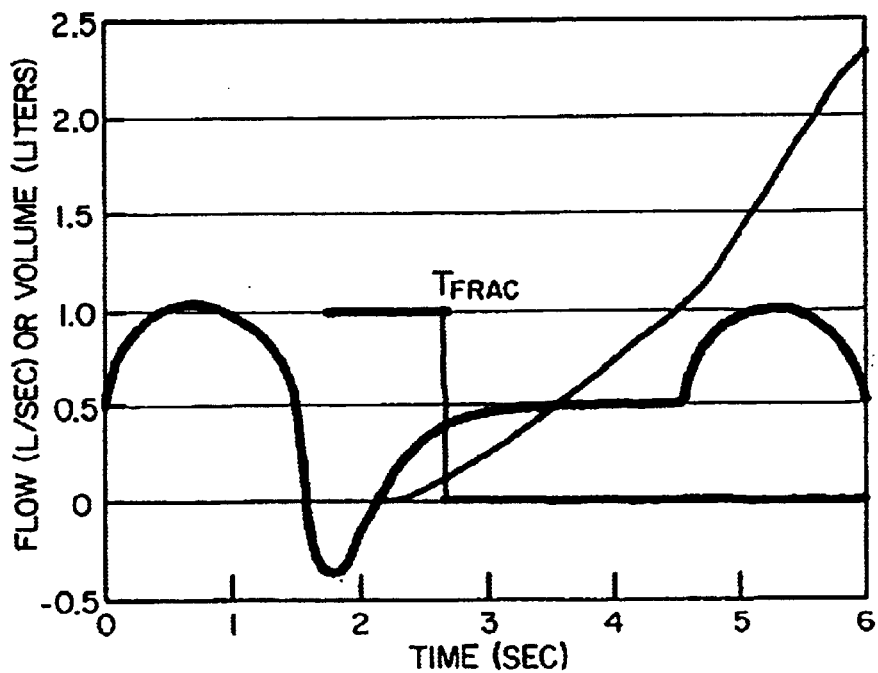
FIG_8B

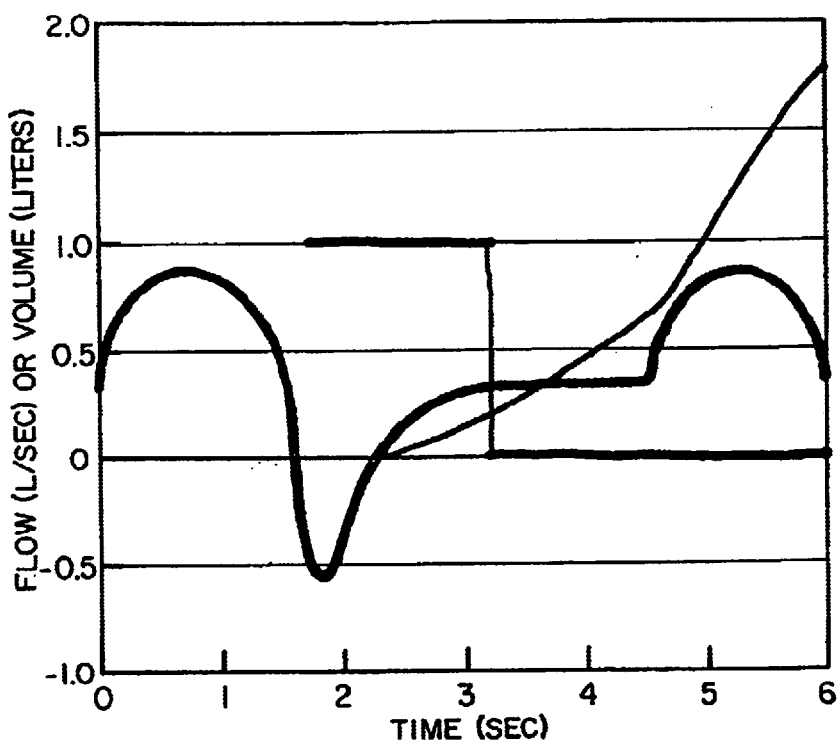
FIG_8C
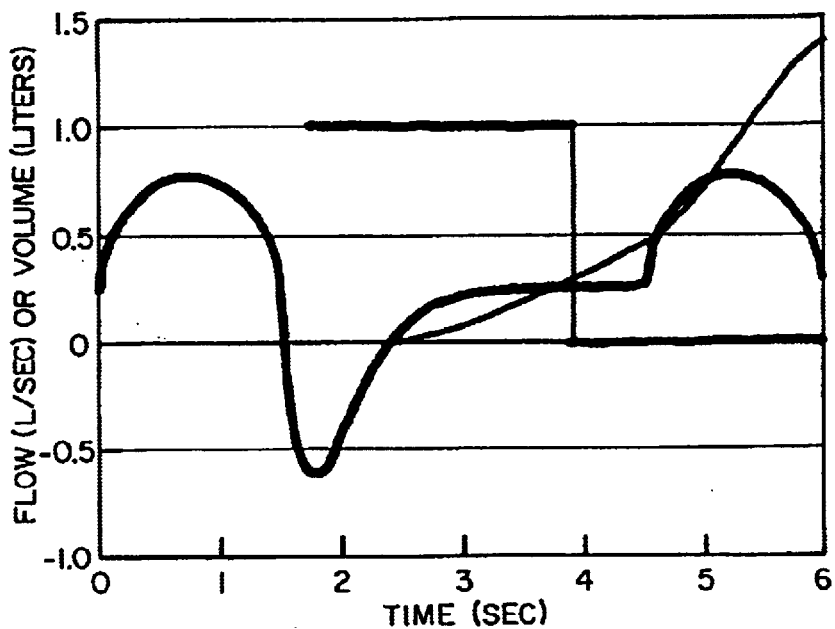
FIG_8D

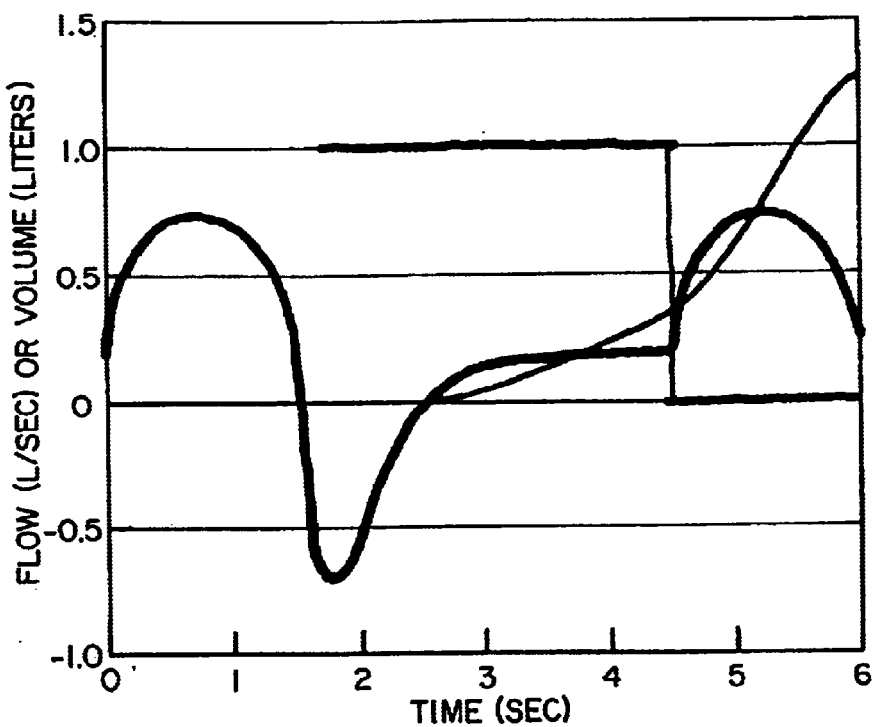
FIG_8E
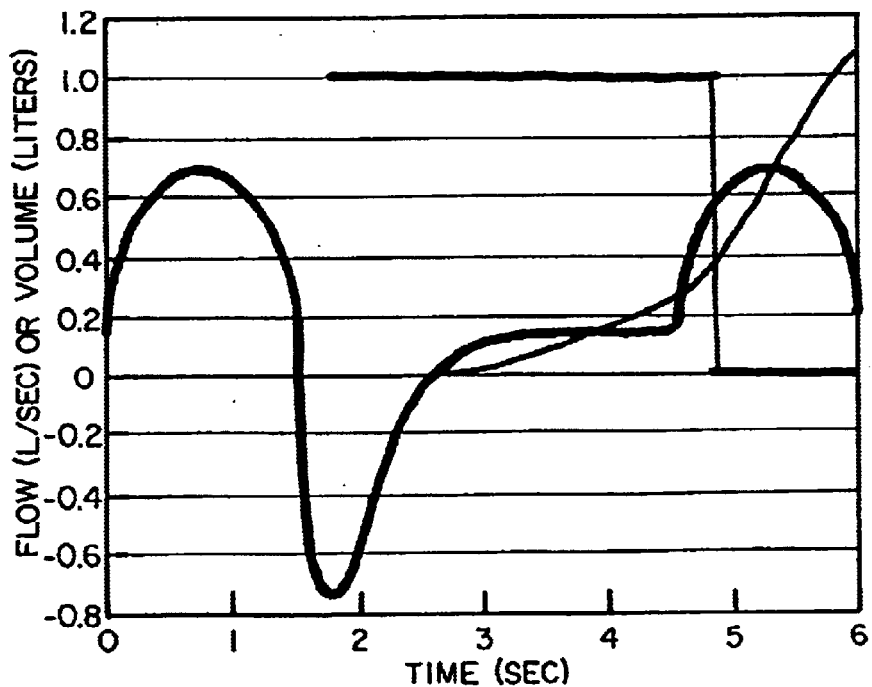
FIG_8F

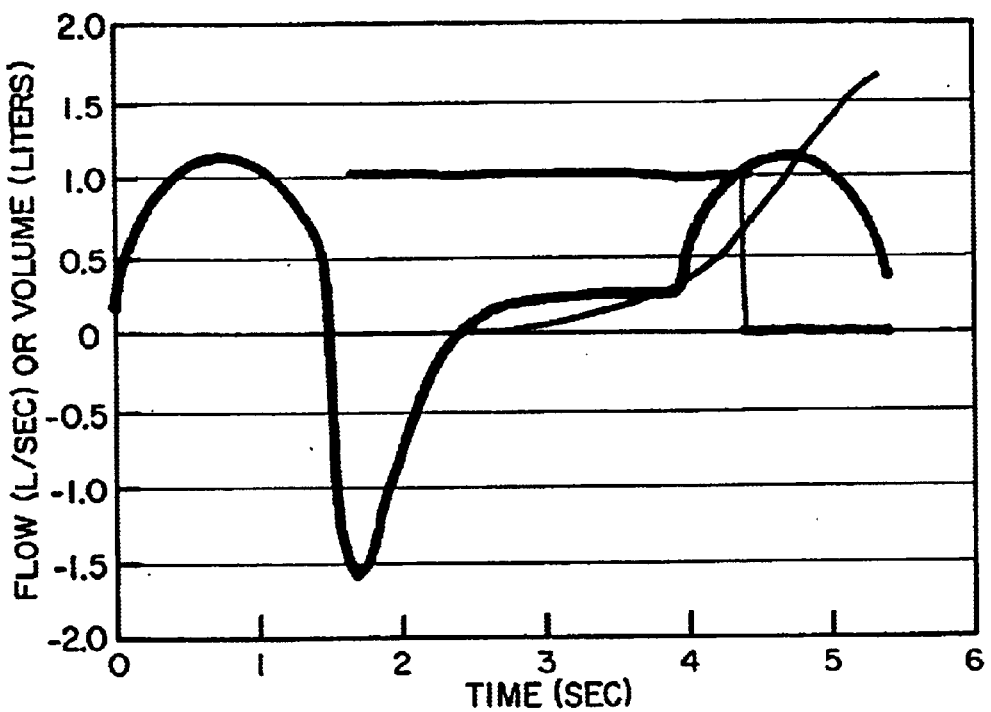
FIG_9A
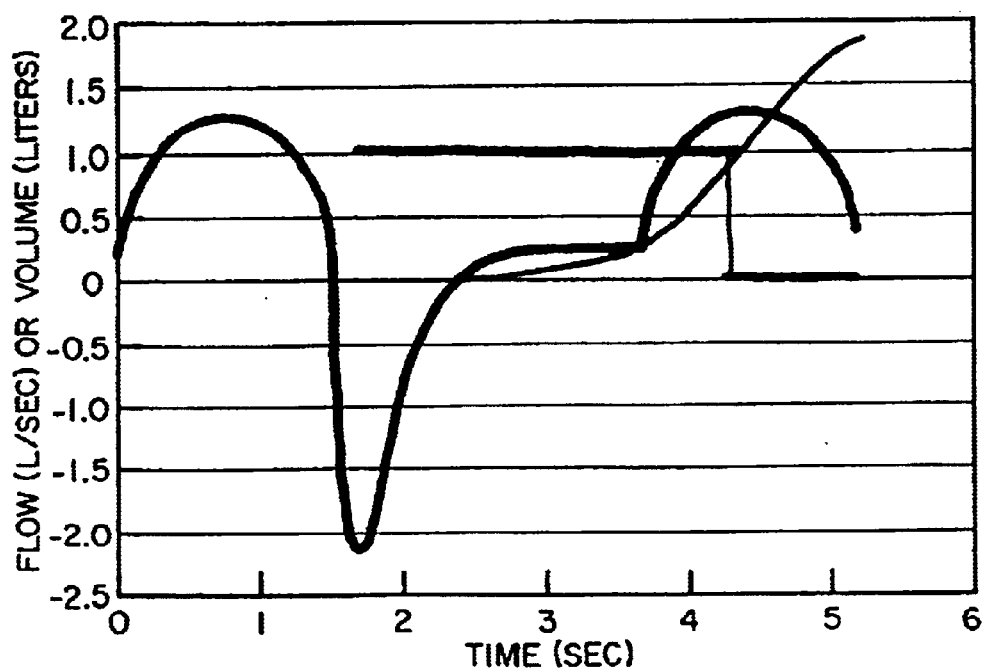
FIG_9B

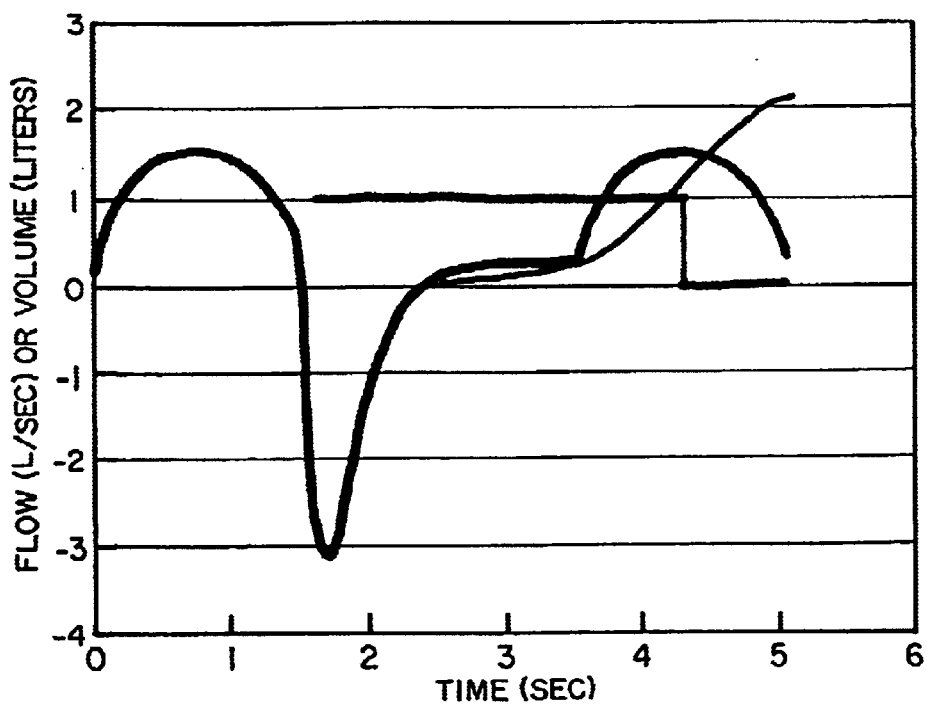
FIG_9C
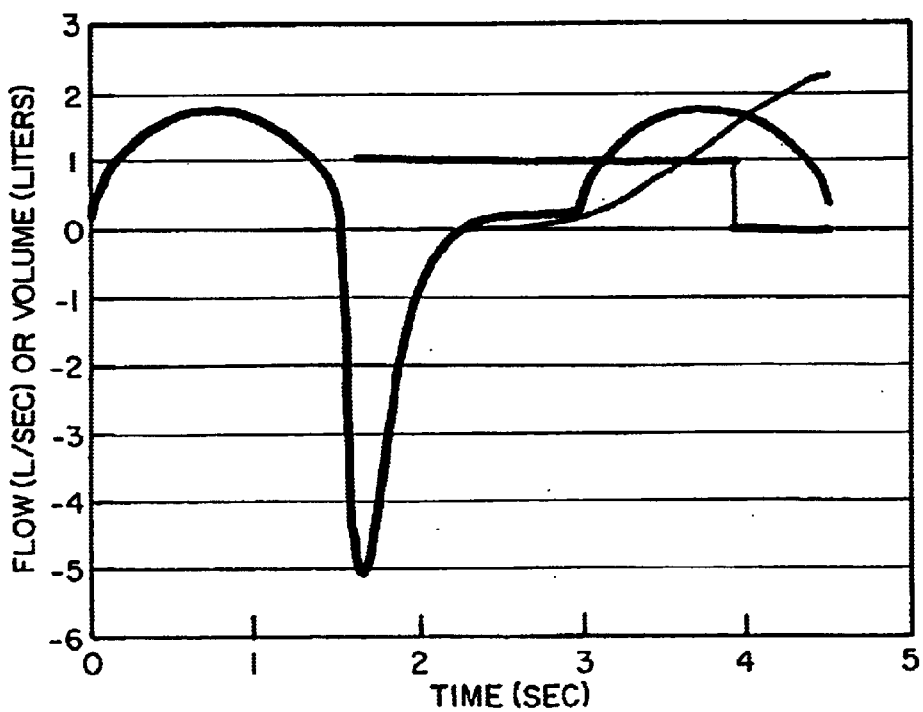
FIG_9D

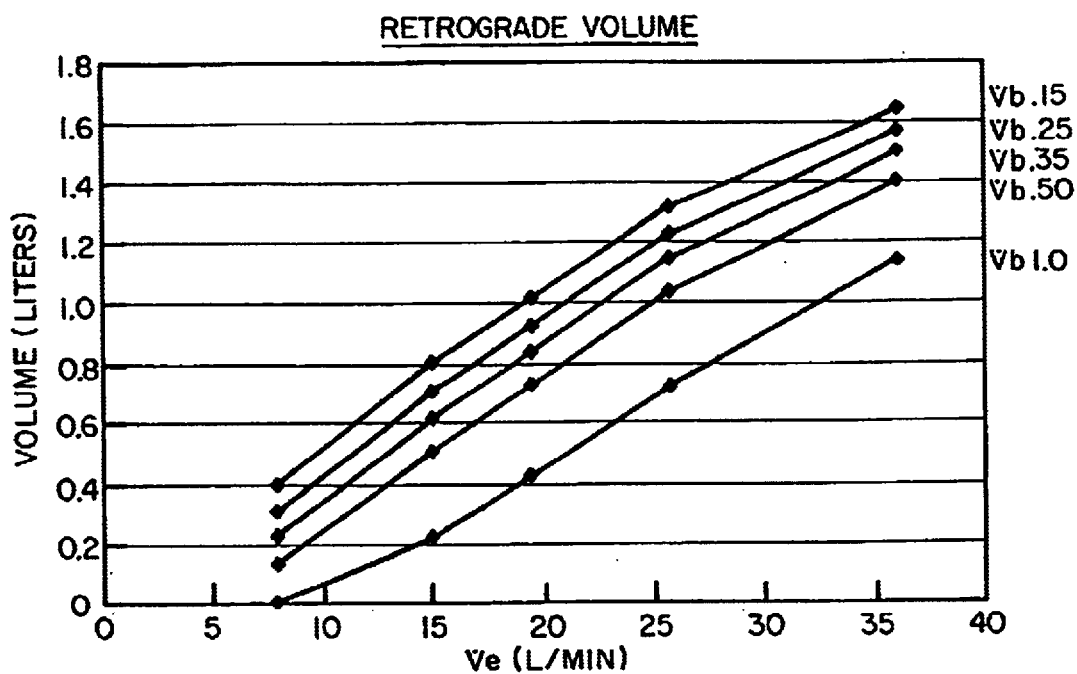
FIG_10
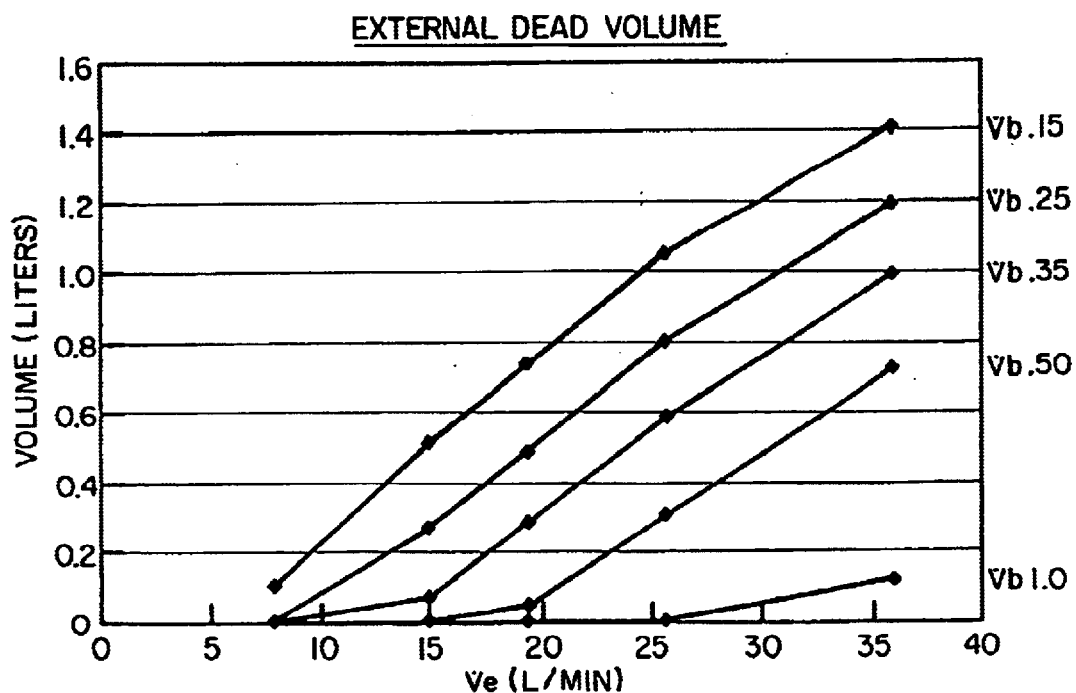
FIG_11

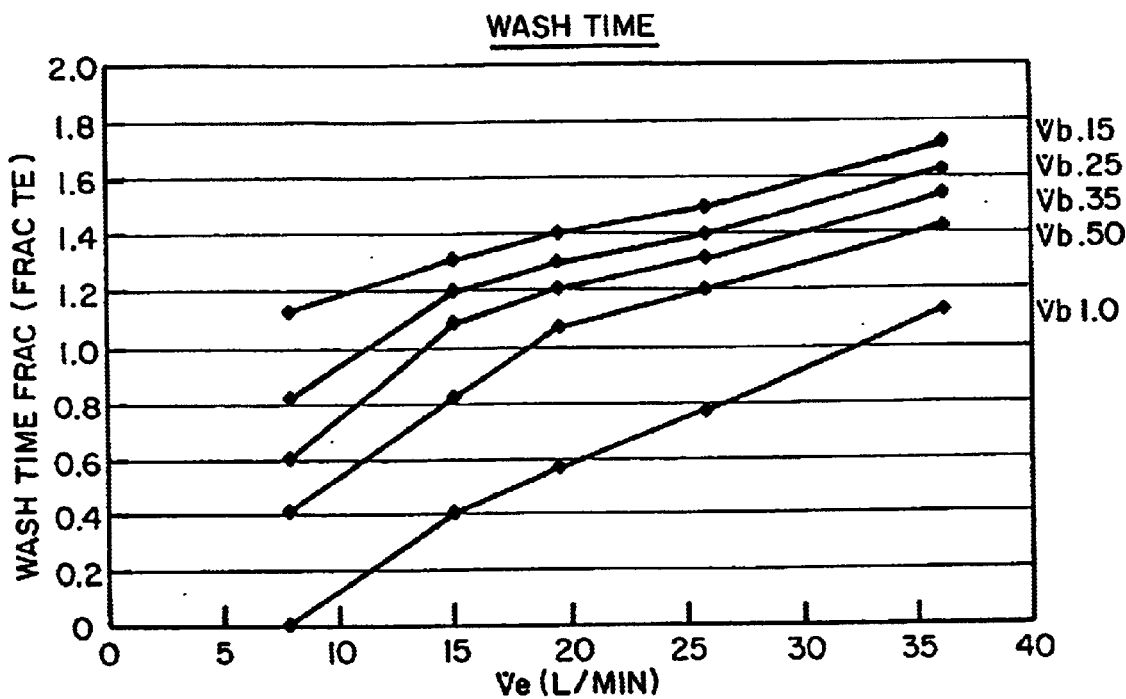
FIG_12
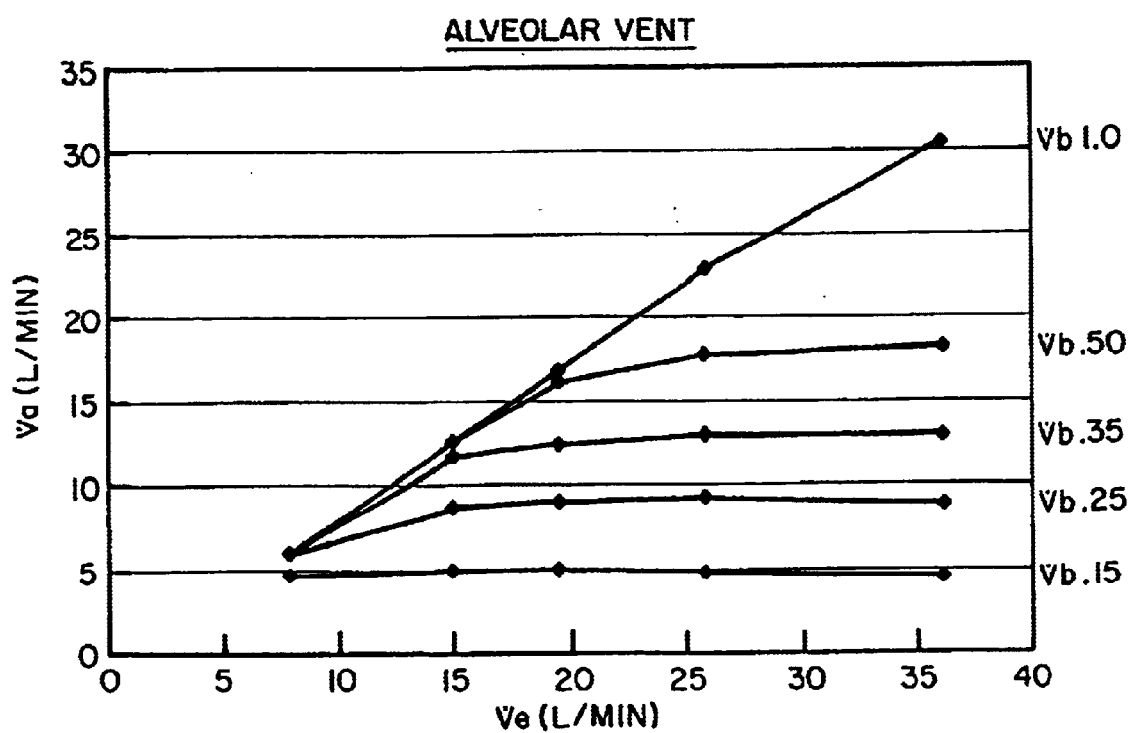
FIG_13

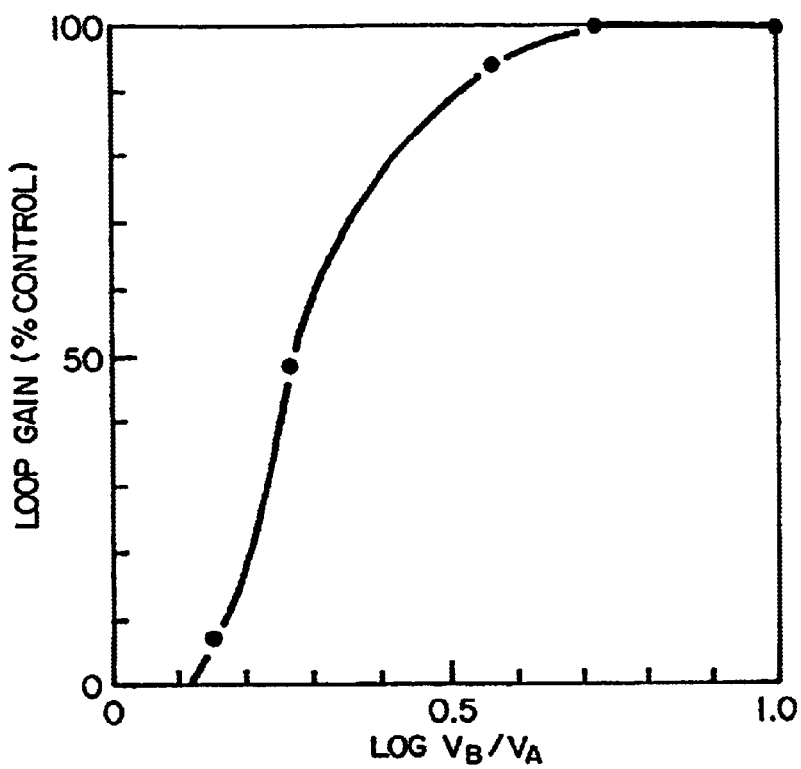
FIG_14
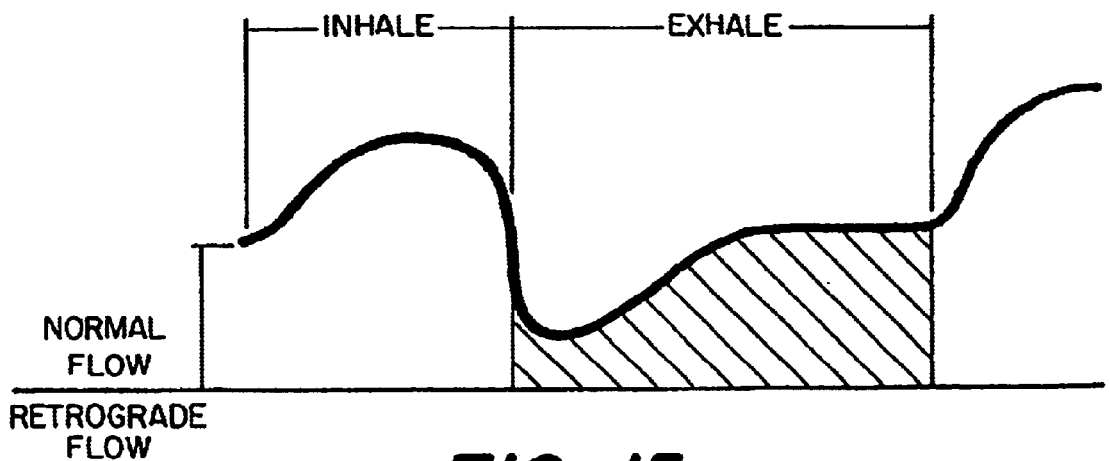
FIG_15
*(PRIOR ART)*

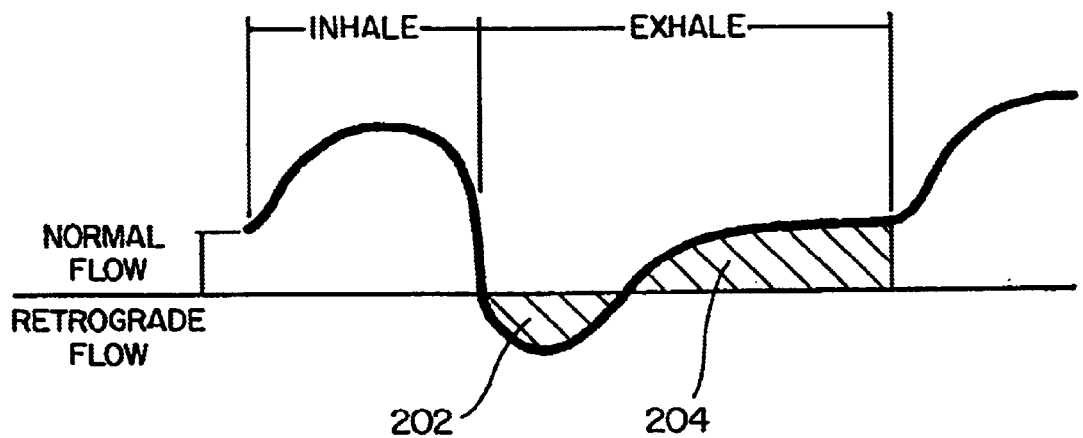
FIG_16
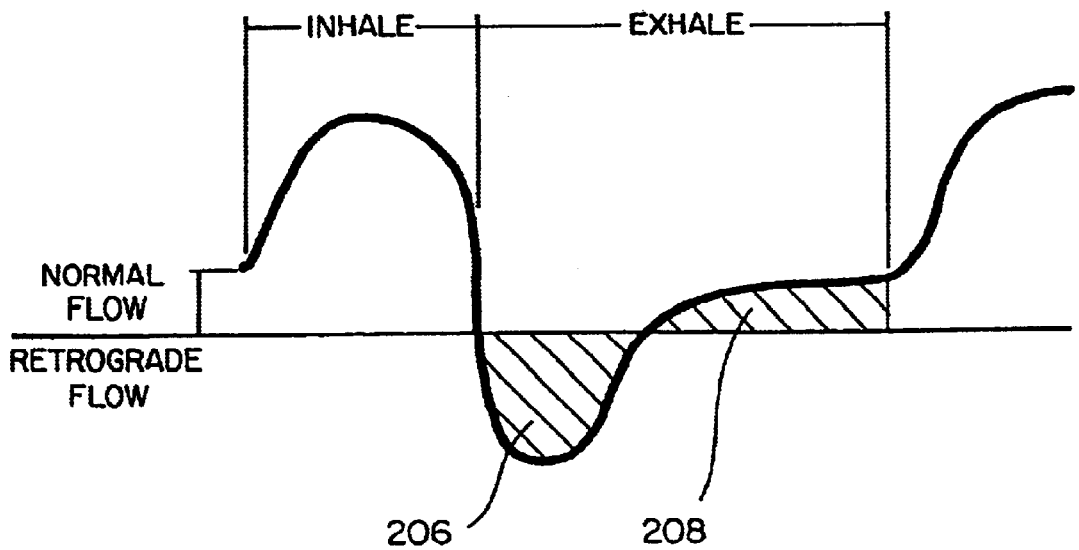
FIG_17

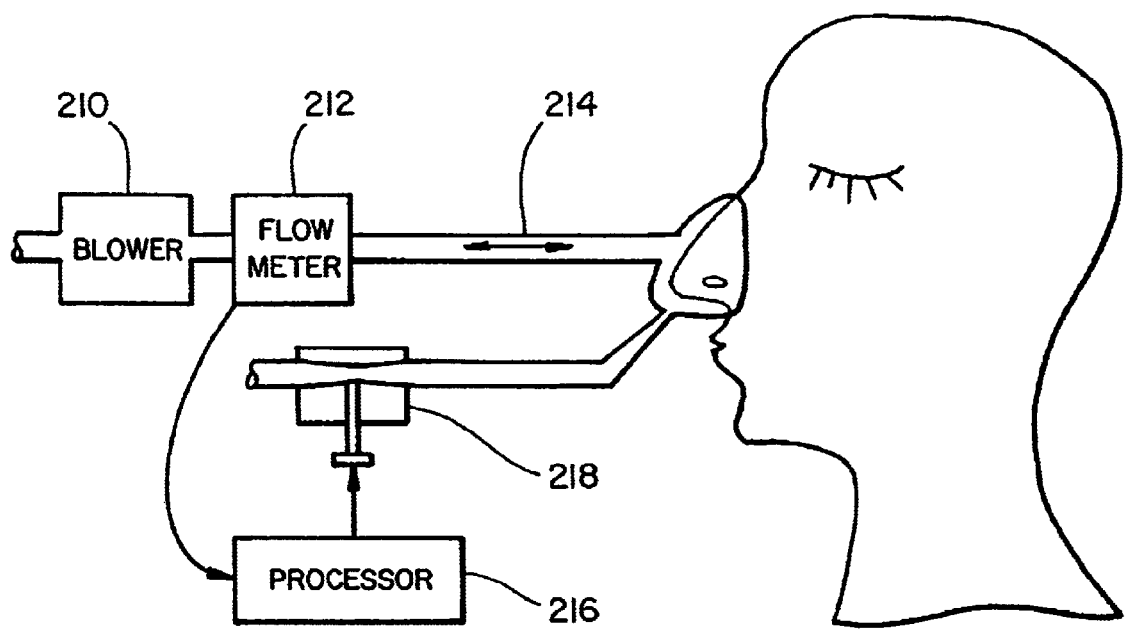
FIG_18A
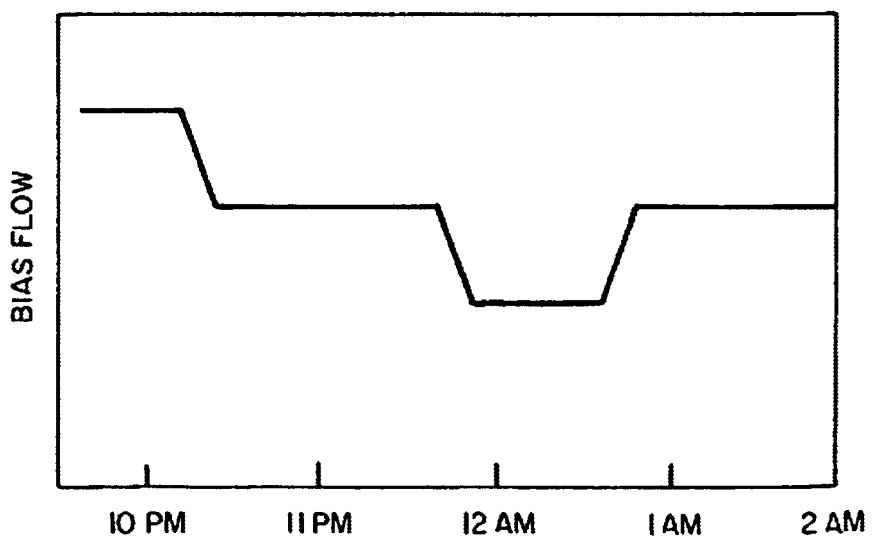
FIG_18B

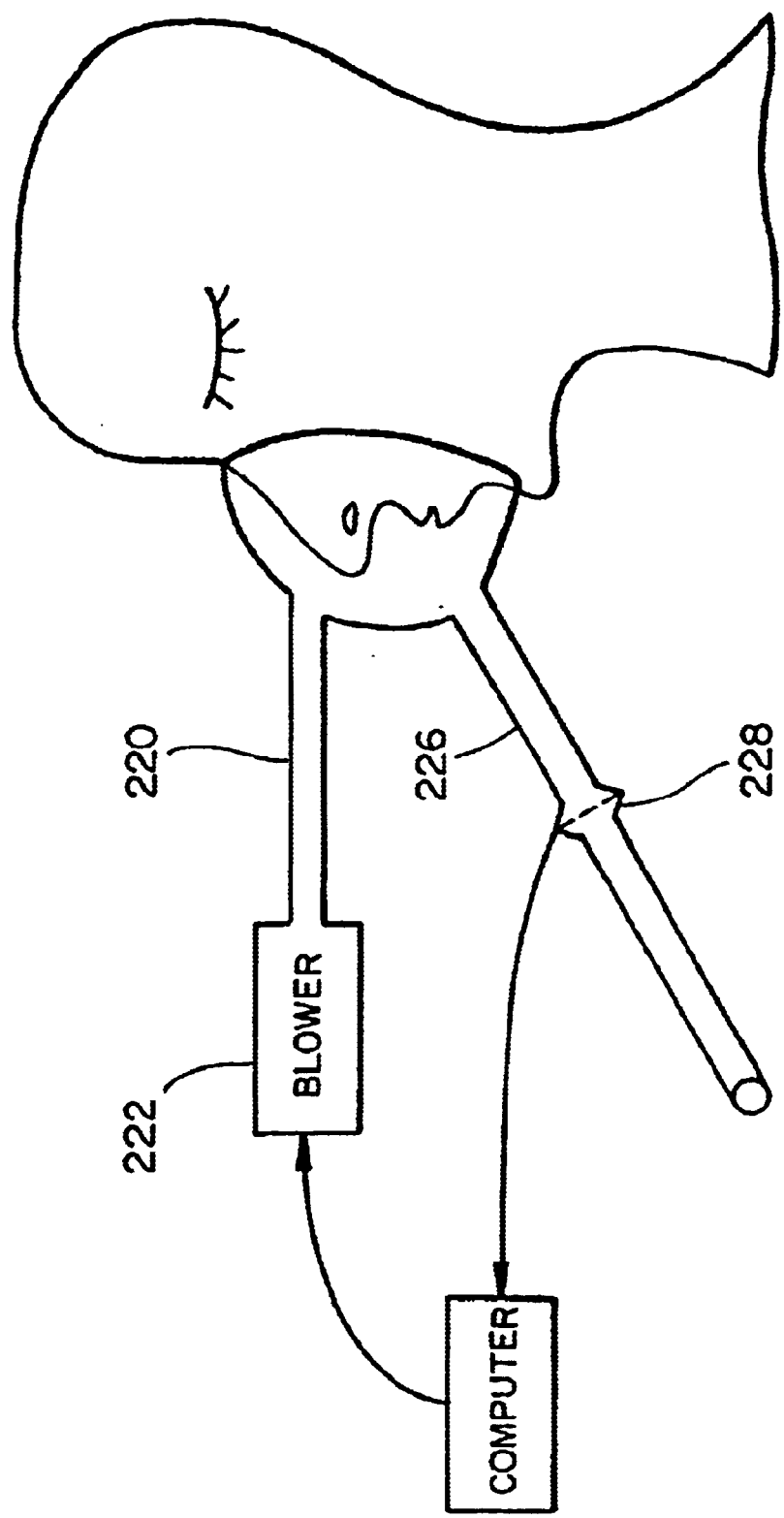
FIG_19

VENTILATORY STABILIZATION TECHNOLOGY

This application claims priority under 35 U.S.C. §§119 and/or 365 to Provision Application No. 60/118,616 filed in the U.S. Patent and Trademark Office on Feb. 4, 1999, the entire content of which is hereby incorporated by reference.

BACKGROUND OF THE INVENTION

Central sleep apnea is a type of sleep-disordered breathing that is characterized by a failure of the sleeping brain to generate regular, rhythmic bursts of neural activity. The resulting cessation of rhythmic breathing, referred to as apnea, represents a disorder of the respiratory control system responsible for regulating the rate and depth of breathing, i.e. overall pulmonary ventilation. Central sleep apnea should be contrasted with obstructive sleep apnea, where the proximate cause of apnea is obstruction of the pharyngeal airway despite ongoing rhythmic neural outflow to the respiratory muscles. The difference between central sleep apnea and obstructive sleep apnea is clearly established, and the two can co-exist. While central sleep apnea can occur in a number of clinical settings, it is most commonly observed in association with heart failure or cerebral vascular insufficiency. An example of central sleep apnea is Cheyne-Stokes respiration.

The respiratory control system comprises a negative feedback system wherein a central pattern generator creates rhythmic bursts of activity when respiratory chemoreceptors sensing carbon dioxide, oxygen and pH are adequately stimulated (FIG. 1). While this neural output of the brainstem central pattern generator to the respiratory muscles derives from a neural rhythm generated intrinsically by the central pattern generator, the generator becomes silent if the feedback signals, related to arterial $P_{CO2}$ and $P_{O2}$, are not sufficiently intense. In other words, the respiratory rhythm is generated by a conditional central pattern generator which requires an adequate input stimulus derived from peripheral chemoreceptors sensing arterial $P_{CO2}$ and $P_{O2}$ from central chemoreceptors sensing brain $P_{CO2}$/pH. Furthermore, the intensity of neural activity generated by the respiratory central pattern generator depends directly upon the arterial $P_{CO2}$ inversely on the arterial $P_{O2}$. Thus, the central and peripheral chemoreflex loops constitute a negative feedback system regulating the arterial $P_{O2}$ and $P_{CO2}$, holding them constant within narrow limits (FIG. 1).

This normal regulation of arterial blood gases is accomplished by a stable ventilatory output of the respiratory central pattern generator. By contrast, central sleep apnea represents an instability of the respiratory control system. The instability can arise from one of two mechanisms, namely: (1) intrinsic failure of the respiratory central pattern generator in the face of adequate stimulation by respiratory chemoreceptors; or (2) lack of adequate stimulation of the central pattern generator by respiratory chemoreceptors. The former is referred to as the "intrinsic instability" and the latter is referred to as the "chemoreflex instability." Theoretically, both mechanisms can co-exist. The common form of central sleep apnea is thought to be caused by the chemoreflex instability mechanism.

The chemoreflex control of breathing might exhibit instability either because the delay of the negative feedback signal is excessively long or because the gain of the system is excessively high. Current evidence indicates that the latter constitutes the principal derangement in central sleep apnea caused by heart failure. Specifically, the overall response of the control system to a change in arterial $P_{CO2}$ is three-fold higher in heart-failure patients with central sleep apnea than in those having no sleep-disordered breathing. This increased gain probably resides within the central chemoreflex loop; however, high gain of the peripheral chemoreflex loop cannot be excluded. Accordingly, the fundamental mechanism of central sleep apnea is taken to be high loop gain of the control system, which results in feedback instability during sleep.

Central sleep apnea causes repeated arousals and oxyhemoglobin desaturations. Although firm evidence linking central sleep apnea to morbidity and mortality is lacking, a variety of evidence leads to the inference that central sleep apnea may promote cardiac arhythmias, strokes, or myocardial infarctions. The repeated nocturnal arousals are likely to impair daytime cognitive function and quality of life. No treatment has become established as being effective for central sleep apnea. Stimulating drugs such as theophyline may be helpful, and carbonic anhydrase inhibitors may relieve central sleep apnea in normals sleeping at high altitude. Nasal continuous positive airway pressure may directly or indirectly improve ventilatory stability. Increasing inspired fractional concentration (F) of oxygen in the inspired gas generally does not eliminate central sleep apnea, whereas increasing inspired $F_{CO2}$ ($F_{ICO2}$=0.01–0.03) promptly eliminates central sleep apnea. However, long-term exposure to high $F_{ICO2}$ would appear to be an undesirable long-term therapy.

SUMMARY OF THE PRESENT INVENTION

The present invention is a method for varying the efficiency of pulmonary gas exchange by using a controlled amount of rebreathing during certain periods of the central sleep apnea respiration cycle so as to counteract the effects of the transient excessive ventilation on the level of carbon dioxide and oxygen in the lungs and in the arterial blood. In effect, this strategy is an attempt to stabilize breathing by minimizing oscillations in the feedback variables.

The invention counteracts periodic breathing due to central sleep apnea by decreasing loop gain of the respiratory control system. In one embodiment, the invention dynamically modulates efficiency of pulmonary gas exchange in relation to pulmonary ventilation. When pulmonary ventilation is stable at resting values, the performance of the system is unchanged. However, during a period of hyperpnea, i.e. when ventilation increases transiently to supra-normal levels, the system is made more inefficient, thus decreasing loop gain and stabilizing the system.

Rebreathing can be used to increase the inspired percentage carbon dioxide and reduce the inspired percentage oxygen just before or during the period of overbreathing. In one embodiment, the patient's ventilation is continuously monitored and analyzed in real time so that the ventilation periodicities of the central sleep apnea breathing can be detected and the inspired carbon dioxide and oxygen concentrations adjusted appropriately by varying the amount of exhaled gas that is reinspired.

In another embodiment of the present invention, a rebreathing apparatus is a part of a nasal continuous positive airway pressure (CPAP) system. The use of continuous positive airway pressure may have a beneficial effect on cardiac function in patients with congestive heart failure. In the future it is likely that patients with congestive heart failure will receive nasal CPAP for treatment of the heart failure. Central sleep apnea may not immediately disappear upon administration of conventional nasal CPAP therapy as central sleep apnea respiration is basically of a nonobstructive origin. However, over a period of about four weeks the degree of heart failure improves; thus, the resulting central sleep apnea respiration may be relieved by the continuous positive airway pressure. This is described in the papers, Naughton, et al., "Effective Continuous Positive Airway Pressure on Central Sleep Apnea and Nocturnal Percentage Carbon Dioxide in Heart Failure," American Journal Respiratory Critical Care Medicine, Vol. 1509, pp 1598–1604, 1994; Naughton, et al., "Treatment of Congestive Heart Failure and Central Sleep Apnea Respiration during Sleep by Continuous Positive Airway Pressure," American Journal of Critical Care Medicine, Vol. 151, pp 92–97, 1995; and, Naughton, et al., "The Role of Hyperventilation in the Pathogenesis of Central Sleep Apneas in Patients with Congestive Heart Failure," American Review of Respiratory Diseases, Vol. 148, pp 330–338, 1993.

It is desirable to have a prompt elimination of the central sleep apnea respiration because the resulting daytime sleepiness and impaired cognition resulting from repeated arousals impair the patient's quality of life. Immediately relieving central sleep apnea breathing during the CPAP treatment would have the advantage that the patient would experience a better sleep and would be more rested. This in turn would enhance compliance with the CPAP treatment program. Conventional nasal CPAP provides no immediate relief of central sleep apnea respiration and resulting arousals.

A conventional CPAP system is modified in one embodiment of the present invention to allow a controlled amount of rebreathing during a portion of the central sleep apnea respiration cycle. In this embodiment, a valve is used to control the amount of rebreathing. When the valve is closed, rebreathing occurs and when the valve is open no rebreathing occurs. A computer connected to a flow meter can be used to detect periodicities in the central sleep apnea respiration cycle. The computer can then control the valve to open and close.

Another embodiment of the present invention concerns a passive low-bias-flow device for treating central sleep apnea. This apparatus includes a gas-supply means, such as a blower, and a mask that is fitted on a patient's face. The gas-supply means is adjusted so that air flow from the gas-supply means is such that for the patient's normal breathing, the gas flow supplied by the gas-supply means is sufficient to prevent a significant amount of the patient's exhaled gases from flowing retrograde into a tube between the gas-supply means and the mask. During periods of increased breathing preceding or following central sleep apnea, the preset air flow is such that some of the patient's exhaled gases flow retrograde into the tube. Some of the exhaled gases flowing retrograde into the tube will be rebreathed by the patient. Thus, during periods of overbreathing associated with central sleep apnea, there will be some rebreathing of gases containing a higher $F_{CO2}$ and a lower $F_{O2}$ than room air. Note that conventional CPAP systems are set such that there is no retrograde air flow any time in the sleep cycle.

Yet another embodiment of the present invention is a method for adjusting an apparatus comprising a gas-supply means, a mask and a tube between the mask and the gas-supply means. In this method, the mask is fitted to the patient's face. The supply of gas from the gas-supply means is set high enough that during the patient's normal breathing, the gas flow supplied by the gas-supply means is sufficient to prevent a significant amount of the patient's exhaled gases from flowing retrograde into the tube, but set low enough that during periods of increased breathing increased with central sleep apnea, some of the patient's exhaled gases flow retrograde into the tube.

Still another embodiment of the present invention concerns an apparatus for treating central sleep apnea wherein the supply of gas from a gas-supply means has a varying gas pressure that changes at different times during the patient's sleep cycle. In this way, rebreathing can be increased. For example, in one embodiment, the gas pressure from the blower is decreased during periods of increased breathing associated with central sleep apnea so that some of the patient's exhaled gases flow retrograde between the mask and the blower. This approach is less advantageous because users often find the varying mask pressure to be annoying. Also, varying of the mask pressure can affect the internal dead space in a manner counter to the rebreathing effect.

The general approach is that the blower pressure is set at a minimum level that eliminates all evidence of upper airway obstruction, or at a level deemed appropriate for treating heart failure. The bias flow is then reduced to a level that eliminates central sleep apnea without increasing the external dead space during unstimulated breathing. The bias flow can then be fixed at this level or varied systematically within or between cycles of periodic breathing.

BRIEF DESCRIPTION OF THE DRAWINGS

FIG. 1 is a diagram illustrating central sleep apnea.

FIG. 2 is a diagram illustrating one embodiment of the rebreathing apparatus of the present invention.

FIG. 3 is a diagram illustrating central sleep apnea respiration.

FIG. 4A is a diagram of one embodiment of the present invention using a passive loop gain modulation for ventilization stabilization using a single pre-set gas flow pressure from a blower.

FIG. 4B is a diagram of an alternate embodiment of the system of FIG. 4A using a flow meter and a computer.

FIG. 5 is a diagram of one embodiment of the present invention which uses computer control of the blower pressure to modify the vent pressure from the blower during certain periods of a sleep cycle.

FIG. 6 is a diagram of an embodiment of the present invention which uses computer control of a dead space attached to valves so as to cause rebreathing during certain periods of a sleep cycle.

FIG. 7 is a diagram of one embodiment of the present invention using a recirculator to increase rebreathing during certain periods of a sleep cycle.

FIGS. 8A–8F are diagrams depicting air flow accorded in tubing connecting between the blower and the nose mask.

FIG. 9 depicts the changes in $V_{ret}$ and $V_{wash}$ that occur when pulmonary ventilation is stimulated by increasing arterial $P_{CO2}$.

FIGS. 10, 11 and 12 are diagrams that illustrate the dependence of $V_{ret}$, $V_{ED}$ and $T_{FRAC}$ on $\dot{V}_E$.

FIG. 13 is a diagram that illustrates the relationship of $\dot{V}_A$ and $\dot{V}E$ at the four levels of $\dot{V}_B$.

FIG. 14 is a diagram illustrating the general dependence of the loop gain on the ratio log $\dot{V}_E/\dot{V}_A$.

FIG. 15 is a diagram that illustrates the breathing air flow in the tube of a conventional CPAP system FIG. 16 is a diagram that illustrates the normal breathing flow in the tube of the embodiment of FIG. 4A.

FIG. 17 is a diagram that illustrates overbreathing flow in the tube in the embodiment of FIG. 4A.

FIG. 18A is a diagram of an embodiment of the present invention in which the size of the exit tube of the mask is varied slowly over the patient's sleep cycle.

FIG. 18B is a graph illustrating one example of changing of the exit hole size during the night, for the apparatus of FIG. 18A.

FIG. 19 is a diagram of an alternate embodiment using the blower output as an active control device to adjust the level of rebreathing by a patient.

DETAILED DESCRIPTION OF THE PREFERRED EMBODIMENT

Figure 2A:
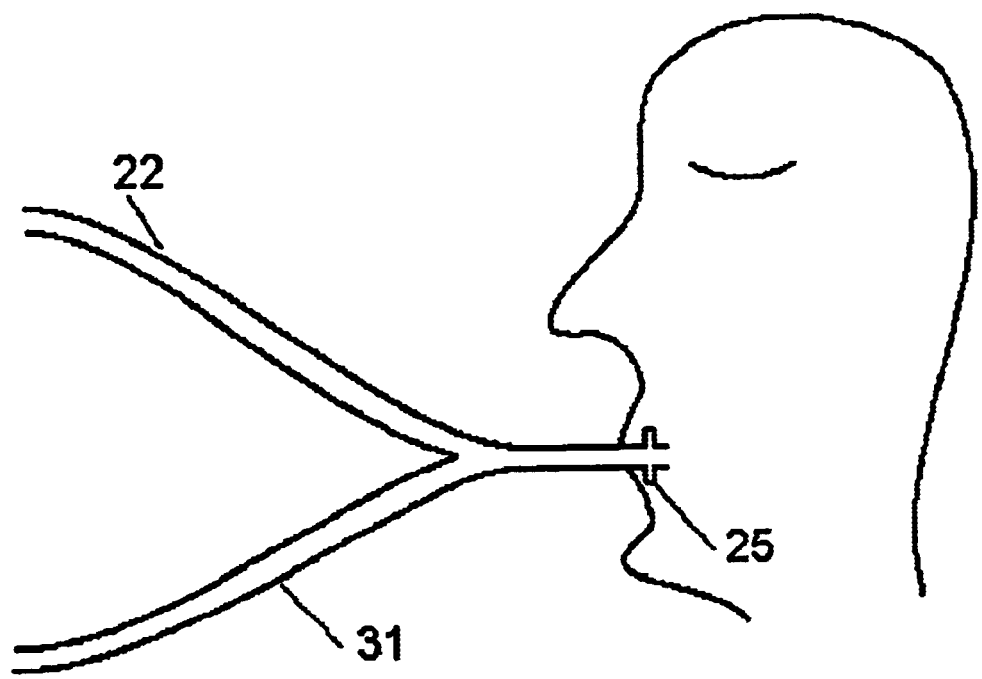
FIG. 2A is a diagram illustrating use of the embodiment of FIG. 2 with a dental appliance.

FIG. 2 is a diagram illustrating the rebreathing apparatus of one active control embodiment of the present invention. In this embodiment, a continuous positive airway pressure apparatus including blower 20, tube 22 and mask 24 is used. Mask 24 preferably produces an airtight tight seal to the face for use in the continuous positive airway pressure treatment. A discussion of continuous positive airway pressure and a preferred continuous positive airway pressure apparatus is described in Remmers, et al. U.S. Pat. No. 5,645,053, "Auto-CPAP Systems and Method for Preventing Patient Disturbance Using Airflow Profile Information." In conventional CPAP, a blower is used to maintain a relatively high constant pressure in a mask and to provide a bias flow of fresh air from the blower out the mask.

In one embodiment of the present invention, tube 26 is connected to the exhaust port 31 of the mask and conducts gas to the variable resistor 28. Alternatively, the valve can be located on the exhaust port of the mask. Tube 22 is used as a dead space for rebreathing during some periods of the central sleep apnea respiration. When the valve 28 is open, no rebreathing occurs because all the exhaled gas is carried out tube 26 through valve 28 by the bias flow before inspiration occurs. When valve 28 is closed, the bias flow ceases and no expired air is conducted through tube 26. In this case, some partial rebreathing occurs because the expired air is conducted retrograde up tube 22 to the blower. The gases in the tube 26 have a higher concentration of carbon dioxide and a lower concentration of oxygen than room air. When the patient inspires, gas is conducted from the blower to the patient and the previously expired gases are inhaled by the patient.

Normally, the bias flow of gas from the blower through the mask and out port 30 would be adequate to completely purge the system during the expiratory phase of the respiratory cycle so that no gas expired by the patient remains in the system. Thus, the gas inspired by the patient had a composition of room air ($O_2$ concentration 21%; $CO_2$ concentration about 0%). Conversely, if the bias flow is reduced to zero by completely. occluding port 30 with valve 28, the gas exhaled by the patient would fill the tube 22 connecting the mask to the blower. Such expired gas would typically have a carbon dioxide concentration of 5% and an oxygen concentration of 16%. Upon inhalation, the patient would first inspire the high carbon dioxide, low oxygen mixture filling the tube, followed by inhalation of room air from the blower. Depending upon the length of the tubing this mixture could amount to rebreathing of 20 to 60 percent of the tidal volume. By varying the exhaust port outflow resistance, the degree of rebreathing between these limits can be varied and the inspired concentration of carbon dioxide and oxygen can be manipulated. In one embodiment, flow meter 32 connected to computer 34 is used to detect the flow of gases to and from the blower 20. The computer 34 is used to identify the periodicities in pulmonary ventilation caused by the central sleep apnea respiration and to control the valve 28 to cause rebreathing during certain periods of the central sleep apnea cycle.

The gas flow from the blower comprises the bias flow (mask exit flow +leak flow) plus the respiratory airflow. The computer monitors this flow and calculates the bias flow, leak flow, retrograde flow, retrograde expired volume and wash volume.

A computer 34 can detect the amplitude of the central sleep apnea cycle and to adjust the resistance of the valve 28 according. For example, if there are large variations in pulmonary ventilation during the central sleep apnea cycle, the valve 28 can be completely closed during the overbreathing period. If there are small variations in pulmonary ventilation during the central sleep apnea cycle, the valve 28 can be partially open during the overbreathing period. Thus, a higher level of rebreathing will occur when the variation in pulmonary ventilation during the central sleep apnea cycle is high than will occur when the variation in pulmonary ventilation during the central sleep apnea cycle is low.

Because of the low impedance of the CPAP blower 20, variations of the resistance in the outflow line cause very little change in mask pressure. Accordingly, the full range of variations in outflow resistance can be made without producing significant deviations in the desired CPAP mask pressure.

The flow meter 32 and computer 34 can quantitate the level of pulmonary ventilation. For example, the ratio of breath volume to breath period gives an indication of the level of the instantaneous pulmonary ventilation. Other indices such as mean or peak inspiratory flow rate could also be used.

FIG. 3 shows an idealized diagram of the periodicities of the overbreathing and underbreathing during central sleep apnea respiration. This diagram shows the regions of overbreathing 50a and the regions of underbreathing 50b compared to the moving time average of ventilation. The computer system will be able to determine the periodicities of the central sleep apnea breathing. Typically, there is about a 50–60 second periodicity to the overbreathing and underbreathing in the central sleep apnea breathing.

A number of techniques are used to control the degree and timing of rebreathing with the valve 28 in order to eliminate central sleep apnea. One way of controlling rebreathing so as to reduce the central sleep apnea respiration is to anticipate the different cycles in the central sleep apnea respiration. For example, looking at FIG. 3, at time A, the system will anticipate a period of overbreathing and thus begin rebreathing by closing valve 28 as shown in FIG. 2. By the time overbreathing portion 50a occurs, there is some level of rebreathing. Because of this, pulmonary gas exchange becomes less efficient during the period of overbreathing and, thereby, the resulting rise in lung oxygen and fall in lung carbon dioxide will be less. As a result, the level of oxygen in the blood does not get too high and the level of carbon dioxide does not get too low. This stabilizes the oxygen and carbon dioxide pressures in the arterial blood and thus will reduce the amplitude of subsequent underbreathing or the length of the apnea. At time B, the system will anticipate an underbreathing cycle by opening the valve 28 and rebreathing will no longer occur. The apparatus of the present invention can reduce central sleep apnea rebreathing (line 50) to a lower level as shown in dotted line 60 in FIG. 2. Time A and time B for the beginning and end of the rebreathing can be determined by the computer 34 shown in FIG. 2.

FIG. 4A is a diagram that illustrates a passive loop gain modulation system for use in the present invention. FIG. 4A depicts a system using a gas-supply means such as the air blower 60 connected to a length of input tubing 62 and then to a mask 64. This system uses a simple fixed exit port for the mask. A tubing volume greater than that normally used with obstructive sleep apnea can be used with the present invention. For example, a ten-foot rather than six-foot tubing can be used. The blower 60 preferably has a very low impedance. That is, changes in the air flow do not significantly change the air pressure supplied by the blower. This can help maintain a relatively stable mask pressure even as the tube flow becomes retrograde.

Additionally, in one embodiment, the air blower is able to supply air pressure much lower than conventional CPAP blowers. In one embodiment, the air blower can be adjusted to supply pressures below 4 cm $H_2O$ (preferably 2 cm $H_2O$ or below). The ability to supply such small pressures allows for the retrograde flow as discussed below.

The mask is fitted about the patient's nose. During normal breathing, the air supplied from the blower 60 and tube 62 to the mask 64 does not cause any rebreathing because any exhaled air will be flushed before the next inhale period. During periods of heavy breathing, the preset gas flow pressure is set so that enough exhaled air flows retrograde into the tube such that during the next inhale period some expired gas is rebreathed. In this embodiment, the overbreathing occurs during certain periods of the sleep cycle associated with central sleep apnea. Rebreathing during periods of overbreathing during central sleep apnea tends to reduce the resulting spike in the blood oxygen level. Thus, the period of underbreathing following the overbreathing in the central sleep apnea sleep cycle will also be reduced.

The alternating periods of under- and overbreathing are reduced by the rebreathing which takes place during the periods of overbreathing. The rebreathing attenuates the arterial blood oxygen spike and the reduction in arterial $P_{CO2}$ caused by the overbreathing. Thus, there is less underventilation when the blood reaches the chemoreceptors. Thus, the amplitude of the periodic breathing is reduced.

The embodiment of FIG. 4A is different than the conventional CPAP in that the preset gas flow pressure is lower and/or the mask exit hole is smaller than that used with conventional CPAP systems. By reducing the gas flow pressure from the typical CPAP gas flow pressures, and/or reducing the mask exit hole size, the retrograde flow during the overbreathing periods is produced.

The system of FIG. 4A has the advantage that it does not require active control of the blower pressure. The patient can be checked into a sleep center and the correct blower pressure and mask exit hole size set. Thereafter, the system can be placed on the patient's nose every night without requiring an expensive controller-based system. The preset blower gas pressure depends upon the air flow resistance caused by the exit 64, the normal exhale pressure and the overbreathing exhale pressure. If the gas-supply pressure system is an air blower 60, then by modifying the revolutions per minute of the air blower, the preset gas flow pressure can be set.

The air supply pressure for patients with central sleep apnea but without obstructive sleep apnea can be set at a relatively low level such as below 4 cm $H_2O$. The normal mask exit holes produce the desired effect at these pressures. The end-tidal $F_{CO2}$ and inspired $F_{CO2}$ can be monitored by a $CO_2$ meter 65 with an aspiration line connected to the mask. Importantly, all mouth leaks should be eliminated in order to have expired gas move into the tubing 62. This can be achieved by applying a chin strap, or by using a full arch dental appliance 25 (FIG. 2A) applied to the upper and lower teeth, or both. An alternative approach to difficult mouth leaks is to use a fill face mask covering the mouth as well as the nose. This means that expired gas emanating from the nose or the mouth will travel retrogradely up the tubing 62 toward the blower.

If the patient has an element of obstructive sleep apnea, the mask pressure is increased progressively until all evidence of upper airway obstruction is eliminated. If the patient is receiving nasal CPAP as treatment for heart failure, mask pressure is set at the desired level (typically 8–10 cm $H_2O$). The bias flow (mask hole size) can then be reduced until central sleep apnea is eliminating without adding dead space.

For patients with heart conditions, the mask pressure can be set at the valve suggested by the literature (typically about 10 cm $H_2O$). Then the bias flow is adjusted.

The flow through tube 62 depends upon the difference in pressure between the blower pressure (i.e., pressure at the outlet of the blower) and mask pressure. Blower pressure is set by the revolutions per minute (RPM) of the blower and will be virtually constant because the internal impedance of the blower is very low. When no respiratory airflow is occurring (i.e., at the end of expiration), mask pressure is less than blower pressure by an amount that is dictated by the flow resistive properties of the connecting tube and the rate of bias flow. This is typically 1–2 cm of water pressure difference when bias flow is at 0.5–1.5L/sec. When the mask is applied to the patient and the patient is breathing, mask pressure varies during the respiratory cycle depending upon the flow resistance properties of the connecting tube and the airflow generated by the patient. During inspiration the mask pressure drops, typically 1–2 cm of water, an during expiration pressure may rise transiently a similar amount. During quiet breathing the peak-to-peak fluctuations in mask pressure are less than during heavy breathing or hyperpnea.

Thus, during quiet breathing the mask pressure rises during exhalation and this reduces the driving pressure difference between the blower and the mask, thereby reducing flow in the tube. If the expired tidal volume increases, however, peak expiratory flow will increase and this will be associated with a further increase in mask pressure. If mask pressure increases to equal blower pressure, flow in the tube will stop. When mask pressure exceeds blower pressure, flow in the tube will be in a retrograde direction, i.e., from the mask to the blower. Such retrograde airflow will first occur early in expiration and the volume of air which moves into the connecting tube will be washed out later in expiration as mask pressure declines and flow from the blower to the mask increases. However, if bias flow is low and the tidal volume is large, a large amount of retrograde flow will occur and a large volume of expired gas will move into the tube. Because the bias flow is small, the wash flow purging the tube will be small. In such a case, not all of the retrograde volume will be washed out before the next inspiration. As a consequence, the overall inspired gas will have a somewhat reduced oxygen concentration and an elevated carbon dioxide concentration.

FIGS. 15–17 illustrate the flow in the tube between a blower and a mask. FIG. 15 is a graph that illustrates breathing air flow in the tube of a conventional CPAP system. Note that during the exhale portion, the flow from the blower to the mask always overpowers the exhale pressure such that there is no retrograde flow into the tube.

This is typically done by setting the air blower pressure and exhaust port resistance such that bias flow out of the mask is relatively high and the possibility of retrograde flow is avoided. This normal flow occurs even for the overbreathing associated with central sleep apnea.

FIGS. 16 and 17 are diagrams that illustrate the effect of breathing in systems of the present invention in which the blower pressure and bias flow out of the exit hole of the mask are set such that there is retrograde flow during portions of overbreathing associated with central sleep apnea.

FIG. 16 illustrates the situation in which there is normal breathing. Even with normal breathing, there is some retrograde flow during the period 202. Later in the exhale period the retrograde volume is washed from the tube by the normal flow that occurs during period 204. Thus there is little or no rebreathing during the normal breathing periods. The system of the present invention does not add dead space during the normal breathing periods. This is important because the addition of dead space can increase the concentration of carbon dioxide that is supplied to the bloodstream. It is assumed that if the increased carbon dioxide level persists for multiple days, the body will readjust the internal feedback system an undesirable manner.

FIG. 17 illustrates an embodiment showing overbreathing along with the apparatus of the present invention. In the embodiment of FIG. 17, the overbreathing is such that there is some retrograde flow of exhaled gases, which remain in the tube at the time of the next inhale portion. This means that at the next inhale portion, the patient will reinspire some exhaled gases with the resultant higher concentration of carbon dioxide. Note that in FIG. 17, the initial exhale region 206 is greater than the exhale region 208.

In one embodiment of the present invention, the retrograde flow volume and wash volume for the normal breathing can be used to set the operation of the present invention. In one embodiment, the retrograde volume region 202 should be one-half the size of the wash flow region 204 for normal breathing. Other rules of thumb such as the comparisons of the aveolar ventilation to the bias flow out of the mask and/or comparisons of the washout time to the duration of expiration could also be used to set the operations of the system of the present invention.

FIG. 4B shows the device of FIG. 4A with the addition of a computer 67 and flow meter 69. The flow meter 69 is used to detect the desired air flow in the tube 62. The blower can then be adjusted so that there is retrograde flow during periods of overbreathing and no retrograde flow otherwise. The device of FIG. 4B can be used to calibrate the device of FIG. 4A for an individual patient.

FIGS. 18A and 18B illustrate an embodiment in which the mask exit size is slowly changed over the course of the night. In this embodiment, the blower 210 supplies airflow at a selected pressure. Flowmeter 212 is connected into the tube 214 which allows the flow in the tube 214 to be determined along with additional parameters of the system including the aveolar volume, bias flow, and the like. The processor 216 slowly changes the size of the exit hole using the variable air resistance apparatus 218. Unlike the system of FIG. 2, the size of the variable output resistance 218 is modified slowly over the night.

Looking at FIG. 18B, if the patient has obstructive sleep apnea as well as central sleep apnea, at the beginning of the night the output valve can be set relatively large, increasing the bias flow out of the mask and thus reducing any effect of retrograde into the tube 214. Once the obstructive sleep apnea is reduced, the valve diameter can be slowly decreased, which can cause an increase of retrograde flow into the tube 214 during the overbreathing portion of central sleep apnea and thus can cause rebreathing which can reduce the central sleep apnea. Additional adjustments in the mask valve opening can be made based upon calculations made by the processor 216.

FIG. 5 is an embodiment of the present invention in which the blower 70 is dynamically controlled. A flow meter 72 is placed in the tube 74 between the blower 70 and mask 76. A flow meter can also be placed near the patient's nose. The system of FIG. 5 allows computer control to decrease the blower pressure during certain periods of a sleep cycle. Thus, during periods of heavy breathing, the blower pressure can be reduced to facilitate retrograde flow and rebreathing. This embodiment is less advantageous because of the mixed effects of changes in the mask pressure. By modifying the gas supply pressure supplied by the blower 70, the retrograde flow into the tube 74 can be increased and decreased, as desired.

FIG. 6 is an alternate embodiment of the present invention. In this embodiment, the mask 82 is connected to dead space 84 by computer-controlled valves 86 and 88. The amount of rebreathing during certain period of the sleep cycle can be modified by changing bias flow by opening and closing the valves 86 and 88, thus reducing the central sleep apnea.

FIG. 7 is an embodiment using a recirculator 90. During certain portions of the sleep cycle, the recirculator 90 allowing exhaled air to be drawn in by the recirculator 90 recirculated and supplied to the user at the mask 92. In this manner, the central sleep apnea can be reduced by increasing the rebreathing at selected portions of the sleep cycle.

Technical Description

One embodiment of the invention is applied in the setting of nasal continuous positive pressure (CPAP) therapy. The loop gain of the negative feedback respiratory control system is reduced principally by increasing the volume of external dead space ($V_{ED}$), the common airway through which gas is conducted during inspiration and expiration. The external dead space constitutes an extension of the internal dead space ($V_{ID}$) comprising the airways of the lung and the upper airway. The total dead space ($V_D$) equals the sum of the internal and external dead spaces.

$$V_D = V_{ED} + V_{ID} \quad \text{(Equation 1)}$$

This volume represents an obligatory inefficiency of the control system in that it reduces the portion of the tidal volume ($V_T$) that participates in gas exchange within the lungs. Specifically, the tidal volume is the sum of two components $$V_T = V_D + V_A \quad \text{(Equation 2)}$$

where $V_A$ represents the "alveolar" portion of the tidal volume, i.e. the volume that participates in respiratory gas exchange. Also, $\dot{V}_E = \dot{V}_A + \dot{V}_D$, where the symbols $\dot{V}_E$, $\dot{V}_A$, and $\dot{V}_D$ signify the products $f.V_T$, $f.V_A$ and $f.V_D$ (f represents respiratory frequency). In the negative feedback loop of the respiratory control system (FIG. 1), $\dot{V}_E$ represents the output of the respiratory central pattern generator and $\dot{V}_A$ is a variable which influences arterial blood gas pressures. The link between $\dot{V}_E$ and $\dot{V}_A$ is, of course, $\dot{V}_D$ which is the primary variable manipulated in dynamically controlling loop gain.

Dynamic control of the rebreathing volume is achieved when the patient is breathing through a nasal CPAP apparatus. When using conventional nasal CPAP the nose is covered by a mask which is connected to a pressure-generating source by a length of tubing. The nose mask is flushed continuously by a stream of gas flowing from the pressure source and exiting the exhaust port of the mask. This will be referred to as the bias flow ($\dot{V}_B$) When using nasal CPAP for its traditional application, i.e., treatment of OSA, the rate of exhaust flow is relatively high so that virtually all the expired gas which enters the mask from the nose flows into the mask and out the exhaust port. Because of the relatively high $V_B$ the mask is completely washed out before the next inspiration occurs. Thus, the gas inspired from the mask has a composition equal to that flowing from the blower (typically room air: $F_{|O2}=0.293$; $F_{|CO2}=0.0003$). In this situation, typical for OSA treatment, the nose mask adds no external dead space. The invention dynamically increases $V_{ED}$ by using a lower value of $\dot{V}_B$ and this, in turn, dynamically reduces $\dot{V}_A$ (Equation 2). Thus, the component of pulmonary ventilation effective in gas exchange, alveolar ventilation ($\dot{V}_A$), is altered on a moment-to-moment basis. Since $\dot{V}_A$ determines the values of the feedback variables, arterial $P_{O2}$ and $P_{CO2}$, $\dot{V}_D$ directly influences loop gain (FIG. 1). Thus, the loop gain (L.G.) of the system can be manipulated as below:

$$\downarrow \dot{V}_B \rightarrow \uparrow V_{ED} \rightarrow \dot{V}_A \downarrow L.G. \quad \text{(Equation 3)}$$

Importantly, the increase in $V_{ED}$ occurs only during periods of hyperpnea, as described below. Thus, during normal breathing, no dead space is added to the system.

As secondary strategies, the invention utilizes changes in CPAP pressure to change lung volume and, thereby, influence loop gain of the respiratory control system. In particular, in increase in lung volume decreases loop gain by decreasing the dynamic change in feedback variables (arterial $P_{CO2}$ and $P_{O2}$) when alveolar ventilation changes dynamically. As well, such an increase in lung volume decreases the end-expiratory length of inspiratory muscles, thereby decreasing their force generation during inspiration. Together, both effects of nasal CPAP decrease the loop gain. When CPAP pressure is dynamically varied in synchrony with the periodic breathing cycle, both effects dynamically modulate loop gain. However, experience indicates that, over the range of CPAP pressure of 1–10 cm $H_2O$, these produce a smaller decrease in loop gain than varying $V_D$. Additionally, dynamic changes in $V_D$ are less likely to disturb the sleeper than changes in CPAP pressure. Accordingly, the use of increase in CPAP pressure to decrease lung volume and, thereby, decrease loop gain, represents a supplementary strategy of the present invention.

The patient with central sleep apnea or combined central and obstructive sleep apnea sleeps with a nasal CPAP mask sealed to the face (FIGS. 2, 4A, 4B, 5, 6, 7) Mouth leaks, if present, are eliminated by a chin strap and/or a dental appliance. If this is not adequate, the nose mask is replaced with a full face mask. The nose mask is connected to a positive pressure outlet of a low impedance blower by a tubing, in one embodiment typically 2–3 cm in diameter and 1.5 m long. The bias flow exits the mask either through an orifice of fixed, selectable size (FIGS. 4A, 4B, 5, 6, 7) or through a tubing, in one embodiment (1.5 m long, 1 cm in diameter) connected to a computer-controlled variable resistor (FIG. 2). In such a system, the mask pressure is determined by blower RPM, and the rate of bias flow $\dot{V}_B$ is the resultant of mask pressure and mask outflow resistance. The apparatus shown in FIGS. 2 and 4B includes a pneumotachagraph for measuring flow from the blower. This device is suitable for initial titration or for nightly therapeutic use. Also, a $CO_2$ meter can be added with a sampling catheter connected to the mask. This allows monitoring of end-tidal and inspired $F_{CO2}$. The device shown in FIG. 4A is a simpler version of that shown in FIG. 4B and is suitable for nightly use.

The dynamically variable bias flow device (FIG. 2) allows moment-to-moment adjustment of bias flow with negligible changes in mask pressure. The exhaust resistor can be controlled by an independent observer during a polysomnographic study, or it can be automatically controlled by a computer algorithm. The control of external dead space volume ($V_{ED}$) is either passively adjusted with the exhaust resistance being constant, or actively adjusted with exhaust resistance being varied in time. In the passive adjustment implementation, bias flow is constant in time since a fixed exhaust orifice is used. In the active adjustment, bias flow changes in time owing to the change in resistance of the bias flow resistor.

FIG. 8 depicts airflow recorded in the tubing which connects the blower to the nose mask. Positive values signify airflow from the blower to the mask, and negative values indicate airflow from the mask to the blower. The former is referred to as "wash" airflow since it eliminates expired gas from the mask; the latter is referred to as "retrograde" airflow since it represents expired air flowing in the reverse direction to that which normally occurs during CPAP administration. As shown in FIG. 8A (top panel), airflow in the tubing is equal to the sum of two air flows, $\dot{V}_B$ and respiratory airflow. The former is constant and the latter varies with the respiratory cycle. Inspiratory airflow produces an upward deflection in $\dot{V}$ and expiratory airflow produces a downward deflection in $\dot{V}$. At the end of expiration (upward arrow in FIG. 8A), respiratory airflow equals zero and tubing airflow equals bias airflow which is chosen to be 1.0L/sec in this example. Peak expiratory airflow occurs early in expiration (downward arrow in FIG. 8A) and equals 1.0L/sec in this example. At this time, tubing airflow is zero because peak expiratory airflow equals $\dot{V}_B$.

FIGS. 8A, 8B, 8C, 8D, 8E and 8F depict the changes in tubing airflow that occur as $\dot{V}_B$ is progressively reduced from 1.0L/sec (FIG. 8A) to 0.15L/sec (FIG. 8F). Respiratory airflow is held constant throughout. As $\dot{V}_B$ is reduced from 1.0 to 0.5, 0.35, 0.25, 0.20 and 0.15L/sec (FIGS. 8A, 8B, 8C, 8D, 8E, 8F), retrograde airflow appears during expiration and becomes progressively larger. The volume of air which moves retrogradely during expiration ($V_{ret}$, hatched area) increases progressively as $\dot{V}_B$ is decreased. Conversely, the volume of air which moves from the blower to the mask during expiration ($V_{wash}$, stippled area) decreases as $\dot{V}_B$ is decreased.

The volume of air resident in the mask and tubing at the end of expiration (downward arrow, FIG. 8A) is referred to as residual volume ($V_R$). $V_R$ can be estimated as the difference between $V_{RET} - V_{WASH}$.

$$V_R = V_{RET} - V_{WASH} \quad \text{(Equation 4)}$$

In the first five examples shown in FIG. 3, $V_R$ is negative or equal to zero (FIGS. 8A, 8B, 8C, 8D, 8E), signifying that With this respiratory pattern, there is no added dead space ($V_{ED}=0$). However, if pulmonary ventilation were to increase, $V_{RET}$ would increase and $V_R$ would become positive. Similarly, if the duration of expiration ($T_e$) were to decrease, $V_{WASH}$ would decrease and $V_R$ would become positive. When breathing is stimulated by an increase in arterial $P_{CO2}$ and a decrease in arterial $P_{O2}$, tidal volume increases and $T_e$ decreases. Accordingly, if $\dot{V}_B$ is relatively low (0.35 and 0.25 in this example), chemical stimulation will cause $V_R$ to assume a positive value so that higher levels of pulmonary ventilation will be associated with greater values of $V_R$.

The presence of a positive value for $V_R$ indicates that $V_{ED}$ will assume a finite value (FIG. 8F). However, $V_R$ does not equal $V_{ED}$. During inspiration, gas resident in the mask and tubing flows to one of two places, namely: out the exhaust port or into the respiratory tract. Only the latter constitutes $V_{ED}$. Accordingly, a fraction of $V_R$ will be inspired, that fraction depending on the value of $\dot{V}_B$ relative to the inspiratory flow rate. Use of a high value of $\dot{V}_B$ will minimize $V_{ED}$. Thus, chemical stimulation of breathing causes three changes in the respiratory pattern, an increase in expiratory air flow rate, a decrease in Te, and an increase in inspiratory air flow rate, each of which acts independently to augment $V_{ED}$. Together, they cause a sharp rise in $V_{ED}$ when $\dot{V}_E$ increases by chemical stimulation if the $\dot{V}_B$ is relatively low. FIG. 8B illustrates the time in expiration when the tubing and mask are flushed by fresh, room air. This time is expressed as a fraction of $T_e$ and referred to as $T_{FRAC}$. $T_{FRAC}$ increases progressively as $\dot{V}_B$ decreases. When $T_{FRAC}$ equals 100%, a critical value of $\dot{V}_B$ has been reached; further decreases in $\dot{V}_B$ will produce a finite value of $V_{ED}$.

To calculate $V_{ED}$, the following relationship is used:

$$V_{ED} = V_R - (\dot{V}_B)(t) \quad \text{(Equation 5)}$$

where t defines the time required for $V_R$ to be eliminated from the mask and conducting tubing as shown in FIG. 9. $V_{ED}$ can be calculated by progressively incrementing inspiratory time (t) from zero (the onset of inspiration) and calculating $V_{SUM}$ inspired volume plus exhaust port volume, i.e., $$V_{SUM} = \int_o^1 \dot{V}_1 + \int_o^t \dot{V}_B \quad \text{(Equation 6)}$$

where $V_1$ represents inspiratory flow rate, i.e., total flow minus bias flow during inspiration. The incrementing procedure continues until $V_{SUM}$ equals $V_R$.

FIG. 9 depicts the changes in $V_{RET}$ and $V_{ED}$ that occur when pulmonary ventilation is stimulated by increasing arterial $P_{CO2}$. $\dot{V}_B$ is assumed to equal 0.25L/sec in all cases, and is approximately two times resting $\dot{V}_A$ (5.7L/min). FIG. 8D depicts the respiratory pattern under unstimulated, resting conditions ($\dot{V}_E$ 8.0L/sec). When ventilation is mildly stimulated ($\dot{V}_E$ 15.0L/sec, FIG. 9A), $V_{RET}$ increases and $V_{WASH}$ decreases so that $V_{ED}$ equals 0.26L. Further stimulation of breathing (FIG. 9B) results in $V_{ED}$ equal to 0.47L when $\dot{V}_E$ equals 19.5L/sec, $V_{ED}$ equal to 0.79L when $\dot{V}_E$ equals 25.7L/sec (FIG. 9C) and $V_{ED}$ equal to 1.19L when $\dot{V}_E$ equals 36.7L/sec (FIG. 9D). Note that $T_{FRAC}$ increases progressively as $\dot{V}_E$ increases for a constant $\dot{V}_B$.

The dependence of $V_{RET}$, $V_{ED}$ and $T_{FRAC}$ on $\dot{V}_E$ is shown in FIGS. 10, 11 and 12, respectively, for all four values of $\dot{V}_E$. Each plot shows a family of $\dot{V}_B$ isopleths. $V_{RET}$, $V_D$ and $T_{FRAC}$ show a quasi-linear increase as $V_E$ increases (FIGS. 10, 11, 12 and 13).

FIG. 13 illustrates the relationship between $\dot{V}_A$ and $\dot{V}_E$ at the five levels of $\dot{V}_B$. For values of 1.0L/sec and greater, all points lie on a monotonically ascending curve. However, for lower values of $\dot{V}_B$, the relationship is shifted downward, indicating that an increment in $\dot{V}_E$ caused by an increase in chemical stimulus will cause a smaller increment in $\dot{V}_A$. This implies a reduction in loop gain which can be quantitated as the change in slope of this relationship. Note that at values of $\dot{V}_E$ equal to 0.35L/sec less, $\dot{V}_A$ becomes constant for values of $\dot{V}_F$ greater than 15L/sec. In other words, the invention clamps $\dot{V}_A$ at some maximal value.

FIG. 14 illustrates the overall dependence of loop gain on the ratio, $\log \dot{V}_E/\dot{V}_A$. This ratio, calculated for resting breathing, provides a normalized index of $\dot{V}_E$ for any patient. The relationship is plotted over the range of $\log \dot{V}_E/\dot{V}_A$ from 0 to 1., i.e. over the range of variation in $\dot{V}_E$ where $V_{ED}$ is less than zero under resting conditions. Note that the loop gain decreases steeply as resting $V_{RET}/V_{WASH}$ decreases from 0.5 to 0. For this reason, we select a ratio value of 0.3 for usual application of the method in treating central sleep apnea. In this situation, $\dot{V}_B$ is approximately two times $\dot{V}_A$ and $T_{FRAC}$ equals 80%. This value results in a 50 % decrease in loop gain while providing more than adequate washout of expired gases from the apparatus under resting conditions. Accordingly, loop gain is reduced to a value that stabilizes breathing for many patients with central sleep apnea without any risk of adding external dead space when the patient is breathing normally and having no central sleep apnea.

The goal of the passive dead space method is to apply nasal CPAP with a $\dot{V}_B$ sufficient to produce $V_{ED}=0$ under resting conditions, but such that the $V_{ED}$ will increase with increasing $\dot{V}_E$ sufficient to reduce the loop gain and stabilize breathing. Specifically, during hypopnea or normal breathing, the apparatus produces no gas exchange inefficiency in breathing. However, during hyperpnea, $\dot{V}_{ED}$ increases progressively as $\dot{V}_E$ rises above normal. The net effect is that $V_D$ is dynamically adjusted in keeping with variations in $\dot{V}_E$ such that the periodic fluctuation in $\dot{V}_A$ is attenuated. This means that fluctuations in arterial $P_{O2}$ and $P_{CO2}$ are reduced, so that loop gain of the system is reduced. This acts to stabilize breathing.

The advantage of the passively adjusting dead space device is that loop gain can be reduced by a relatively simple apparatus requiring no active algorithmic, dynamic adjustment in $\dot{V}_B$. Once the effective $\dot{V}_B$ has been determined, this can be achieved by permanent adjustment of the resistance of the exhaust port of the mask, thereby eliminating the need for an exhaust tubing and computer-controlled exhaust resistor. However, if the loop gain of the patient's respiratory control system is very high, the passive apparatus may not reduce the loop gain sufficiently to stabilize breathing. In that case, a dynamically adjusting $V_{ED}$ apparatus is employed. In the embodiment that dynamically adjusts $\dot{V}_B$, the indicator variables ($V_{RET}$, $V_{WASH}$, $T_{frac}$ and $V_B/V_A$) are calculated on line. Periodic breathing is detected either by the recurrence of apneas or by autoregressive analysis. $\dot{V}_B$ is reduced progressively until evidence of central sleep apnea is eliminated or until the indicator variables reach their critical limits ($V_{RET}$, $V_{WASH}=0.8$, $T_{frac}=80\%$ and $\dot{V}_B/\dot{V}_A=2$).

FIG. 19 depicts another embodiment of the invention. The patient with central sleep apnea wears a nose mask or full face mask 220 which can be loose fitting. The mask 220 is purged by a bias flow from a high-impedance blower 222 which supplies a constant rate of airflow to the mask. This bias flow is selectable and rapidly adjustable by the controlling computer 224. The bias flow exits to the atmosphere through a low-resistance reservoir tubing 226. The respiratory airflow (both inspiration and expiration) occurs through this reservoir tubing. Because of the tubing's low resistance, the mask pressure remains near atmospheric pressure. A pneumotachograph (flow meter 228) in the reservoir tubing allows monitoring of bias flow and respiration airflow and calculation of wash volume during expiration and expired tidal volume.

Under resting conditions or when no central sleep apnea respiration is detected, bias flow is held relatively high so that wash voluke exceds the volume of gas expired into the tube. Accordingly, when inspiration begins, the reservoir tube has been washed completely with bias flow, and the patient inspires room air. Thus, no external dead space has been added when the patient is breathing normally and no ventilatory periodicity is detected by the computer. When the computer 222 detects ventilatory periodicity, bias flow is varied in synchrony with the periodicity. Specifically, when instantaneous ventilation is greater than he moving average, bias flow is reduced so that wash volume is less than expired tidal volume. This causes rebreathing and decreases loop gain of the system. During periods of underbreathing, bias flow is maintained at high values so that no rebreathing occurs. The volume of gas resident in the reservoir tubing 226 at the end of expiration (i.e., the rebreathing volume) is calculated on line and is adjusted to be proportional to the difference between instantaneous ventilation and moving average ventilation. Thus, dead space increases progressively as overbreathing occurs, thereby minimizing the effect of the excessive ventilation on arterial blood gases. This, in turn, minimizes the duration of the apnea or magnitude of hypopnea that follows the overbreathing and stabilizes ventilation.

It will be appreciated by those of ordinary skill in the art that the invention can be implemented in other specific forms without departing from the spirit or central character thereof. The presently disclosed embodiments are therefore considered in all respects to be illustrative and not restrictive. The scope of the invention is indicated by the appended claims rather than the foregoing description, and all changes which come within the meaning and range of equivalence thereof are intended to be embraced herein. Accordingly, the above description is not intended to limit the invention, which is to be limited only by the following claims.

What is claimed is:

1. An apparatus for treating central sleep apnea comprising:
    a gas supplying means; and
    a mask adapted to be fit on a patient's face, the mask operably connected using a tube to the gas supplying means, the mask having an exit, wherein the apparatus is arranged such that during periods of increased breathing associated with central sleep apnea, some exhaled gasses from the patient flow retrograde into the tube towards the gas supplying means and away from the exit; wherein the apparatus is adapted such that during an initial exhale portion of increased breathing associated with central sleep apnea, some exhaled gasses from the patient flow retrograde into the tube towards the gas supplying means and away from the exit and wash flow out of the tube such that during a next inhale portion a sufficient amount of rebreathing occurs to control central sleep apnea.

2. The apparatus of claim 1, wherein the apparatus is adapted such that during normal breathing periods little rebreathing occurs.

3. The apparatus of claim 2, wherein the apparatus is adapted such that during normal breathing periods some retrograde flow occurs but wash flow is sufficient to remove exhaled air before a next inhale portion.

4. The apparatus of claim 1, wherein the retrograde flow into the tube is influenced by gas pressure from the gas supplying means and by an exit hole size.

5. The apparatus of claim 1, wherein the exit hole size is adjustable.

6. The apparatus of claim 1, wherein pressure in the mask is set high enough to treat obstructive sleep apnea.

7. The apparatus of claim 1 wherein the gas-supplying means comprises a blower which blows air to the mask.

8. The apparatus of claim 1 wherein the mask is adapted to fit about a patient's nose.

9. The apparatus of claim 1 wherein die gas-supplying means is adjustable.

10. The apparatus of claim 1, wherein gas pressure from the gas supplying means is set below four cm $H_2O$ pressure.

11. The apparatus of claim 1, wherein gas pressure from the gas supplying means is set at two cm $H_2O$ pressure or below.

12. The apparatus of claim 1 in which the mask comprises a dental appliance.

13. An apparatus for treating central sleep apnea comprising:
    a gas supplying means; and
    a mask adapted to be fit on a patient's face, the mask operably connected using a tube to the gas supplying means, the mask having an exit, wherein the apparatus is arranged such that during periods of increased breathing associated with central sleep apnea, some exhaled gasses from the patient flow retrograde into the tube towards the gas supplying means and away from the exit, wherein gas pressure from the gas supplying means is set at a controlled level below four cm $H_2O$ pressure independently of the respiratory cycle of the patient.

14. The apparatus of claim 13, wherein gas pressure from the gas supplying means is set at two cm $H_2O$ pressure or below.

15. The apparatus of claim 13 in which the mask comprises a dental appliance.

16. A method of treating a patient suffering from central sleep apnea, the method comprising:
    providing an apparatus comprising a gas supplying means and a mask adapted to be fit on the patient's face, the mask operably connected using a tube to the gas supplying means, the mask having an exit;
    fitting the mask to the patient's face; and
    adjusting the apparatus such that during periods of increased breathing associated with central sleep apnea, some exhaled gasses from the patient flow retrograde into the tube, wherein the adjusting step is done such that during an initial exhale portion of increased breathing associated with central sleep apnea, some exhaled gasses from the patient flow retrograde into the tube and wash flow out of the tube such that during a next inhale portion some rebreathing occurs sufficient to treat central sleep apnea.

17. The method of claim 16, wherein the adjusting step is done such that during normal breathing periods little rebreathing occurs.

18. The method of claim 17, wherein the adjusting step is done such that during normal breathing periods some retrograde flow occurs but wash flow is sufficient to remove exhaled air before a next inhale portion.

19. The method of claim 16, wherein the retrograde flow into the tube is influenced by gas pressure from the gas supplying means and by an exit hole size.

20. The method of claim 16, wherein the adjusting step includes adjusting an exit hole size.

21. The method of claim 16, wherein pressure in the mask is set high enough to treat obstructive sleep apnea.

22. The method of claim 16, wherein the gas supplying means comprises a blower.

23. The method of claim 16 wherein the mask is fitted about a patient's nose.

24. The method of claim 16, wherein the adjusting step is such that gas pressure from the gas supplying means is set below four cm $H_2O$ pressure.

25. The method of claim 16, wherein the adjusting step is such that gas pressure from the gas supplying means is set at two cm $H_2O$ pressure or below.

26. The method of claim 16 in which the mask comprises a dental appliance.

27. A method of treating a patient suffering from central sleep apnea, the method comprising:
providing an apparatus comprising a gas supplying means and a mask adapted to be fit on the patient's face, the mask operably connected using a tube to the gas supplying means, the mask having an exit;
fitting the mask to the patients face; and
adjusting the apparatus such that during periods of increased breathing associated with central sleep apnea, some exhaled gasses from the patient flow retrograde into the tube wherein the adjusting step is such that gas pressure from the gas supplying means is set at a level below four cm $H_2O$ pressure independently of the respiratory cycle of the patient.

28. The method of claim 27, wherein the adjusting step is such that gas pressure from the gas supplying means is set at two cm $H_2O$ pressure or below.

29. The method of claim 27 in which the mask comprises a dental appliance.

30. An apparatus for treating central sleep apnea comprising:
a gas supplying means;
a mask adapted to be fit on a patient's face, the mask operably connected using an input tube to the gas supplying means, the mask having an exit;
a variable air resistance means operably connected to the exit of the mask; and
a controller operably connected to the variable air resistance means to adjust a level of rebreathing that occurs and maintains a temporally variable flow of air in the input tube without producing significant deviations in mask pressure.

31. The apparatus of claim 30 wherein the variable air resistance means comprises an adjustable valve.

32. The apparatus of claim 31 further comprising an exit tube between the mask and the adjustable valve.

33. The apparatus of claim 30 wherein the controller adjusts the variable air resistance means to provide a dead space during certain portions of a sleep cycle.

34. The apparatus of claim 30 wherein the controller adjusts the variable air resistance means to modify exit flow out of the mask at different times during a nights sleep.

35. The apparatus of claim 30 further comprising a flow meter to provide signals to the controller.

36. The apparatus of claim 30 wherein the controller detects periodicities in sleep cycle to determine how to adjust the level of rebreathing.

37. The apparatus of claim 30 in which the mask comprises a dental appliance.

38. An apparatus for treating central sleep apnea comprising:
a gas supplying means;
a mask adapted to be fit on a patient's face, the mask incorporating a dental appliance to reduce mouth leaks, the mask operably connected using a tube to the gas supplying means; and
a processor adapted to adjust a level of rebreathing to control central sleep apnea in the patient by adjusting an active control element of the apparatus, wherein the active control element is selected from the group consisting of (1) a variable air resistance means operably connected to an exit of the mask, (2) a recirculator, and (3) a valve to a dead space volume.

39. The apparatus of claim 38, wherein the active control element is a unit to adjust a blower output.

40. The apparatus of claim 39, wherein the active control element is a unit to adjust a blower output revolutions per minute.

41. The apparatus of claim 38, wherein the active control element is adjusted during a periodic sleep cycle of the patient.

42. The apparatus of claim 38, wherein the active control element is adjusted over an entire sleeping period.

43. The apparatus of claim 38, wherein the processor receives data from a flow meter.

44. The apparatus of claim 38, wherein the processor receives data from a carbon dioxide sensor.

45. An apparatus for treating central sleep apnea comprising:
a gas supplying means;
a mask adapted to be fit on a patient's face, the mask incorporating a dental appliance to reduce mouth leaks, the mask operably connected using a tube to the gas supplying means;
a processor adapted to adjust a level of rebreathing to control central sleep apnea in the patient by adjusting an active control element of the apparatus; and
an exit tube connected to the mask.

46. An apparatus for treating central sleep apnea comprising:
a blower; and
a mask adapted to be fit on a patient's face, the mask operably connected using a tube to the blower, the mask having an exit, tile resistance of the exit being set that during treatment of central sleep apnea in the patient, expiratory air from the patient flows through the tube towards the blower and away from the exit, wherein the apparatus is arranged such that a gas flow from the blower is less than that used to treat obstructive sleep apnea.

47. The apparatus of claim 46, wherein gas pressure from the blower is set at four cm $H_2O$ pressure or below.

48. The apparatus of claim 47, wherein gas pressure from the blower is set at two cm $H_2O$ pressure or below.

49. The apparatus of claim 46, wherein the apparatus is arranged such that during periods of increased breathing associated with central sleep apnea, some exhaled gasses from the patient flow retrograde into the tube.

50. The apparatus of claim 49, wherein the apparatus is adapted such that during an initial exhale portion of increased breathing associated with central sleep apnea, some exhaled gasses from the patient flow retrograde into the tube and wash flow out of the tube such that during a next inhale portion some rebreathing occurs.

51. The apparatus of claim 49, wherein the apparatus is adapted such that during normal breathing periods little rebreathing occurs.

52. The apparatus of claim 49, wherein the apparatus is adapted such that during normal breathing periods some retrograde flow occurs but wash flow is sufficient to remove exhaled air before a next inhale portion.

53. The apparatus of claim 46 wherein the blower is adjustable.

54. A method of treating a patient suffering from central sleep apnea, the method comprising:
providing an apparatus comprising a blower and a mask adapted to be fit on the patient's face, the mask operably connected using a tube to the blower, the mask having an exit;
fitting the mask to the patient's face; and
adjusting the apparatus such that gas flow from the blower is controlled at a variable flow rate and essentially constant pressure, the pressure being less than that used to treat obstructive sleep apnea, in order to treat central sleep apnea in the patient, and such that during periods of increased breathing associated with central sleep apnea, some exhaled gasses from the patient flow retrograde into the tube.

55. The method of claim 54, wherein the adjusting step is such that gas pressure from the blower is set below four cm $H_2O$ pressure.

56. The method of claim 55, wherein the adjusting step is such that gas pressure from the blower is set at two cm $H_2O$ pressure or below.

57. The method of claim 54, wherein the adjusting step is done such that during an initial exhale portion of increased breathing associated with central sleep apnea, some of the patient's exhaled gasses flow retrograde into the tube and wash flow out of the tube such that during a next inhale portion some rebreathing occurs.

58. The method of claim 54, wherein the adjusting step is done such that during normal breathing periods little rebreathing occurs.

59. Te method of claim 58, wherein the adjusting step is done such that during normal breathing periods some retrograde flow occurs but wash flow is sufficient to remove the exhaled air before a next inhale portion.

60. The method of claim 54, wherein the retrograde flow into the tube is influenced by gas pressure from the blower and by an exit hole size.

61. The method of claim 54 in which the mask comprises a dental appliance.

62. A method comprising:
providing an apparatus comprising a blower and a mask adapted to be fit on a patient's face, the mask operably connected using a tube to the blower, the mask having an exit;
fitting the mask to the patient's face;
detecting central sleep apnea in the patient; and
adjusting the apparatus to treat central sleep apnea, wherein the adjusting step is such that during periods of increased breathing associated with central sleep apnea, some exhaled gasses flow from the patient retrograde into the tube.

63. The method of claim 62, wherein the adjusting step comprises adjusting the apparatus such that gas flow from the blower is less than that used to treat obstructive sleep apnea to treat central sleep apnea in the patient.

64. The method of claim 62, wherein the adjusting step is such that gas pressure from the blower is set below four cm $H_2O$ pressure.

65. The method of claim 64, wherein the adjusting step is such that gas pressure from the blower is set at two cm $H_2O$ pressure or below.

66. The method of claim 63, wherein the adjusting step is done such that during an initial exhale portion of increased breathing associated with central sleep apnea, some of the patient's exhaled gasses flow retrograde into the tube towards the blower and away from the exit and wash flow out of the tube such that dining a next inhale portion some rebreathing occurs.

67. The method of claim 63, wherein the adjusting step is done such that during normal breathing periods little rebreathing occurs.

68. The method of claim 67, wherein the adjusting step is done such that during normal breathing periods some retrograde flow occurs but wash flow is sufficient to remove exhaled air before a next inhale portion.

69. The method of claim 62, wherein the retrograde flow into the tube is influenced by gas pressure from the blower and by a size of an exit hole size, and gas flow rate from the blower is varied without significantly affecting mask pressure.

70. The method of claim 62, further comprising an obstructive sleep apnea treating step.

71. The method of claim 70, wherein the obstructive sleep apnea treating step occurs before the adjusting step.

72. A method comprising:
providing an apparatus comprising a blower and a mask adapted to be fit on a patient's face, the mask operably connected using a tube to the blower, the mask having an exit, the resistance of the exit being set that during treatment of central sleep apnea in the patient, expiratory air from the patient flows through the tube towards the blower and away from the exit;
fitting the mask to the patient's face;
treating an obstructive sleep apnea with the apparatus;
adjusting the apparatus to treat central sleep apnea; and
treating obstructive sleep apnea with the apparatus.

73. The method of claim 72, wherein the adjusting step comprises adjusting the apparatus such that gas flow from the blower is less than that used to treat obstructive sleep apnea to treat central sleep apnea in the patient.

74. The method of claim 72, wherein the adjusting step is such that gas pressure from the blower is set below four cm $H_2O$ pressure.

75. The method of claim 74, wherein the adjusting step is such that gas pressure from the blower is set at two cm $H_2O$ pressure or below.

76. The method of claim 72 wherein the adjusting step is such that during periods of increased breathing associated with central sleep apnea, some of the patient's exhaled gasses flow retrograde into the tube.

77. The method of claim 76, wherein the adjusting step is done such that during an initial exhale portion of increased breathing associated with central sleep apnea, some exhaled gasses from the patient flow retrograde into the tube and wash flow out of the tube such that during a next inhale portion some rebreathing occurs.

78. The method of claim 76, wherein the adjusting step is done such that during normal breathing periods little rebreathing occurs.

79. The method of claim 78, wherein the adjusting step is done such that during normal breathing periods some retrograde flow occurs but wash flow is sufficient to remove exhaled air before a next inhale portion.

80. The method of claim 72, wherein the retrograde flow into the tube is influenced by gas pressure from the blower and by a size of the exit hole.

81. The method of claim 72, wherein the obstructive sleep apnea treating step comprises supplying blower pressure greater than eight cm $H_2O$.

82. The method of claim 72, wherein the obstructive sleep apnea treating step occurs before the adjusting step.

* * * * *